(12) United States Patent
Sgroi, Jr.

(10) Patent No.: US 11,123,101 B2
(45) Date of Patent: Sep. 21, 2021

(54) RETAINING MECHANISMS FOR TROCAR ASSEMBLIES

(71) Applicant: Covidien LP, Mansfield, MA (US)

(72) Inventor: Anthony Sgroi, Jr., Wallingford, CT (US)

(73) Assignee: Covidien LP, Mansfield, MA (US)

( * ) Notice: Subject to any disclaimer, the term of this patent is extended or adjusted under 35 U.S.C. 154(b) by 166 days.

(21) Appl. No.: 16/503,838

(22) Filed: Jul. 5, 2019

(65) Prior Publication Data
US 2021/0000500 A1      Jan. 7, 2021

(51) Int. Cl.
*A61B 17/34* (2006.01)

(52) U.S. Cl.
CPC ...... *A61B 17/3421* (2013.01); *A61B 17/3476* (2013.01); *A61B 2017/347* (2013.01); *A61B 2017/348* (2013.01); *A61B 2017/3435* (2013.01)

(58) Field of Classification Search
CPC ...... A61B 17/1155; A61B 2017/00486; A61B 17/115; A61B 17/3421; A61B 17/3476; A61B 2017/00371; A61B 2017/00384; A61B 2017/0046; A61B 2017/00473; A61B 2017/00477; A61B 2017/0053; A61B 2017/00862; A61B 2017/07257; A61B 2017/07271; A61B 2017/3435; A61B 2017/347; A61B 2017/348; A61B 17/3423; A61B 17/3439; A61B 17/3468;
(Continued)

(56) References Cited

U.S. PATENT DOCUMENTS

| 2,777,340 A | 1/1957 | Hettwer et al. |
| 2,957,353 A | 10/1960 | Babacz |
| 3,111,328 A | 11/1963 | Di Rito et al. |
| (Continued) | | |

FOREIGN PATENT DOCUMENTS

| CA | 908529 A | 8/1972 |
| CA | 2451558 A1 | 1/2003 |
| (Continued) | | |

OTHER PUBLICATIONS

European Search Report dated Nov. 27, 2020, issued in corresponding EP Appln. No. 20183904, 12 pages.
(Continued)

*Primary Examiner* — Robert A Lynch
*Assistant Examiner* — Alyssa M Keane
(74) *Attorney, Agent, or Firm* — Carter, DeLuca & Farrell LLP

(57) ABSTRACT

An adapter assembly includes a sleeve, a trocar assembly releasably securable within the sleeve, and a retaining mechanism configured to releasably secure the trocar assembly within the sleeve. The retaining mechanism includes a retaining block, a cam wire moveably positioned relative to the retaining block between a lock position and a release position, a retaining block extension for maintaining the cam wire relative to the retaining block, a button member in operable engagement with the cam wire, and a pair of retaining members. The button member includes a center beam moveable from an unflexed position in engagement with a stop tab of the retaining block extension to prevent movement of the button member to a flexed position out of alignment with the stop tab to permit movement of the button member.

20 Claims, 15 Drawing Sheets

(58) Field of Classification Search
CPC .... A61B 2017/3443; A61B 2017/3445; A61B 2017/3482; A61B 2017/00464
See application file for complete search history.

(56) References Cited

U.S. PATENT DOCUMENTS

| | | |
|---|---|---|
| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |
| 3,695,058 A | 10/1972 | Keith, Jr. |
| 3,734,515 A | 5/1973 | Dudek |
| 3,759,336 A | 9/1973 | Marcovitz et al. |
| 3,771,526 A | 11/1973 | Rudie |
| 4,162,399 A | 7/1979 | Hudson |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,705,038 A | 11/1987 | Sjostrom et al. |
| 4,708,141 A | 11/1987 | Inoue et al. |
| 4,717,063 A | 1/1988 | Ebihara |
| 4,722,685 A | 2/1988 | de Estrada et al. |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,823,807 A | 4/1989 | Russell et al. |
| 4,873,977 A | 10/1989 | Avant et al. |
| 4,874,181 A | 10/1989 | Hsu |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,129,118 A | 7/1992 | Walmesley |
| 5,129,570 A | 7/1992 | Schulze et al. |
| 5,139,513 A | 8/1992 | Segato |
| 5,152,744 A | 10/1992 | Krause et al. |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,301,061 A | 4/1994 | Nakada et al. |
| 5,309,927 A | 5/1994 | Welch |
| 5,312,023 A | 5/1994 | Green et al. |
| 5,312,024 A | 5/1994 | Grant et al. |
| 5,314,435 A | 5/1994 | Green et al. |
| 5,314,436 A | 5/1994 | Wilk |
| 5,326,013 A | 7/1994 | Green et al. |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,350,355 A | 9/1994 | Sklar |
| 5,355,897 A | 10/1994 | Pietrafitta et al. |
| 5,360,154 A | 11/1994 | Green |
| 5,368,215 A | 11/1994 | Green et al. |
| 5,383,874 A | 1/1995 | Jackson et al. |
| 5,383,880 A | 1/1995 | Hooven |
| 5,389,098 A | 2/1995 | Tsuruta et al. |
| 5,392,979 A | 2/1995 | Green et al. |
| 5,395,030 A | 3/1995 | Kuramoto et al. |
| 5,395,033 A | 3/1995 | Byrne et al. |
| 5,400,267 A | 3/1995 | Denen et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,413,267 A | 5/1995 | Solyntjes et al. |
| 5,425,738 A | 6/1995 | Gustafson et al. |
| 5,427,087 A | 6/1995 | Ito et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,467,911 A | 11/1995 | Tsuruta et al. |
| 5,470,006 A | 11/1995 | Rodak |
| 5,474,223 A | 12/1995 | Viola et al. |
| 5,476,379 A | 12/1995 | Disel |
| 5,487,499 A | 1/1996 | Sorrentino et al. |
| 5,497,934 A | 3/1996 | Brady et al. |
| 5,503,635 A | 4/1996 | Sauer et al. |
| 5,518,163 A | 5/1996 | Hooven |
| 5,518,164 A | 5/1996 | Hooven |
| 5,522,534 A | 6/1996 | Viola et al. |
| 5,526,822 A | 6/1996 | Burbank et al. |
| 5,529,235 A | 6/1996 | Boiarski et al. |
| 5,533,661 A | 7/1996 | Main et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,562,239 A | 10/1996 | Boiarski et al. |
| 5,588,579 A | 12/1996 | Schnut et al. |
| 5,609,285 A | 3/1997 | Grant et al. |
| 5,626,587 A | 5/1997 | Bishop et al. |
| 5,626,591 A | 5/1997 | Kockerling et al. |
| 5,632,432 A | 5/1997 | Schulze et al. |
| 5,632,433 A | 5/1997 | Grant et al. |
| 5,639,008 A | 6/1997 | Gallagher et al. |
| 5,641,111 A | 6/1997 | Ahrens et al. |
| 5,645,209 A | 7/1997 | Green et al. |
| 5,647,526 A | 7/1997 | Green et al. |
| 5,653,374 A | 8/1997 | Young et al. |

(56) References Cited

U.S. PATENT DOCUMENTS

| | | |
|---|---|---|
| 5,658,300 A | 8/1997 | Bito et al. |
| 5,662,662 A | 9/1997 | Bishop et al. |
| 5,667,517 A | 9/1997 | Hooven |
| 5,669,918 A | 9/1997 | Balazs et al. |
| 5,685,474 A | 11/1997 | Seeber |
| 5,693,042 A | 12/1997 | Boiarski et al. |
| 5,704,534 A | 1/1998 | Huitema et al. |
| 5,709,335 A | 1/1998 | Heck |
| 5,713,505 A | 2/1998 | Huitema |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,792,573 A | 8/1998 | Pitzen et al. |
| 5,797,536 A | 8/1998 | Smith et al. |
| 5,799,857 A | 9/1998 | Robertson et al. |
| 5,814,055 A | 9/1998 | Knodel et al. |
| 5,820,009 A | 10/1998 | Melling et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,863,159 A | 1/1999 | Lasko |
| 5,868,760 A | 2/1999 | McGuckin, Jr. |
| 5,881,943 A | 3/1999 | Heck |
| 5,908,427 A | 6/1999 | McKean et al. |
| 5,915,616 A | 6/1999 | Viola et al. |
| 5,947,363 A | 9/1999 | Bolduc et al. |
| 5,951,576 A | 9/1999 | Wakabayashi |
| 5,954,259 A | 9/1999 | Viola et al. |
| 5,957,363 A | 9/1999 | Heck |
| 5,964,774 A | 10/1999 | McKean et al. |
| 5,993,454 A | 11/1999 | Longo |
| 5,993,468 A | 11/1999 | Rygaard |
| 6,010,054 A | 1/2000 | Johnson et al. |
| 6,017,354 A | 1/2000 | Culp et al. |
| 6,024,748 A | 2/2000 | Manzo et al. |
| 6,032,849 A | 3/2000 | Mastri et al. |
| 6,045,560 A | 4/2000 | McKean et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,090,123 A | 7/2000 | Culp et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,126,651 A | 10/2000 | Mayer |
| 6,129,547 A | 10/2000 | Cise et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,239,732 B1 | 5/2001 | Cusey |
| 6,241,139 B1 | 6/2001 | Milliman et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,264,087 B1 | 7/2001 | Whitman |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,338,737 B1 | 1/2002 | Toledano |
| 6,343,731 B1 | 2/2002 | Adams et al. |
| 6,348,061 B1 | 2/2002 | Whitman |
| 6,368,324 B1 | 4/2002 | Dinger |
| 6,371,909 B1 | 4/2002 | Hoeg et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,434,507 B1 | 8/2002 | Clayton et al. |
| 6,439,446 B1 | 8/2002 | Perry et al. |
| 6,443,973 B1 | 9/2002 | Whitman |
| 6,450,390 B2 | 9/2002 | Heck et al. |
| 6,461,372 B1 | 10/2002 | Jensen et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,537,280 B2 | 3/2003 | Dinger et al. |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,610,066 B2 | 8/2003 | Dinger et al. |
| 6,611,793 B1 | 8/2003 | Burnside et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,645,218 B1 | 11/2003 | Cassidy et al. |
| 6,652,542 B2 | 11/2003 | Blatter et al. |
| 6,654,999 B2 | 12/2003 | Stoddard et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,699,177 B1 | 3/2004 | Wang et al. |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,783,533 B2 | 8/2004 | Green et al. |
| 6,792,390 B1 | 9/2004 | Burnside et al. |
| 6,793,652 B2 | 9/2004 | Whitman et al. |
| 6,817,508 B1 | 11/2004 | Racenet et al. |
| 6,820,791 B2 | 11/2004 | Adams |
| 6,821,282 B2 | 11/2004 | Perry et al. |
| 6,827,246 B2 | 12/2004 | Sullivan et al. |
| 6,830,174 B2 | 12/2004 | Hillstead et al. |
| 6,840,423 B2 | 1/2005 | Adams et al. |
| 6,843,403 B2 | 1/2005 | Whitman |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,852,122 B2 | 2/2005 | Rush |
| 6,860,892 B1 | 3/2005 | Tanaka et al. |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,899,538 B2 | 5/2005 | Matoba |

(56) References Cited

U.S. PATENT DOCUMENTS

| | | |
|---|---|---|
| 6,905,057 B2 | 6/2005 | Swayze et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,959,852 B2 | 11/2005 | Shelton, IV et al. |
| 6,964,363 B2 | 11/2005 | Wales et al. |
| 6,978,922 B2 | 12/2005 | Bilotti et al. |
| 6,981,628 B2 | 1/2006 | Wales |
| 6,981,941 B2 | 1/2006 | Whitman et al. |
| 6,981,979 B2 | 1/2006 | Nicolo |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,331 B2 | 6/2006 | Adams et al. |
| 7,059,508 B2 | 6/2006 | Shelton, IV et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,111,769 B2 | 9/2006 | Wales et al. |
| 7,114,642 B2 | 10/2006 | Whitman |
| 7,118,528 B1 | 10/2006 | Piskun |
| 7,122,029 B2 | 10/2006 | Koop et al. |
| 7,122,044 B2 | 10/2006 | Bolduc et al. |
| 7,128,748 B2 | 10/2006 | Mooradian et al. |
| 7,140,528 B2 | 11/2006 | Shelton, IV |
| 7,141,049 B2 | 11/2006 | Stern et al. |
| 7,141,055 B2 | 11/2006 | Abrams et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,168,604 B2 | 1/2007 | Milliman et al. |
| 7,172,104 B2 | 2/2007 | Scirica et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,225,964 B2 | 6/2007 | Mastri et al. |
| 7,234,624 B2 | 6/2007 | Gresham et al. |
| 7,235,089 B1 | 6/2007 | McGuckin, Jr. |
| 7,238,021 B1 | 7/2007 | Johnson |
| 7,246,734 B2 | 7/2007 | Shelton, IV |
| 7,252,660 B2 | 8/2007 | Kunz |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,328,828 B2 | 2/2008 | Ortiz et al. |
| 7,334,718 B2 | 2/2008 | McAlister et al. |
| 7,335,212 B2 | 2/2008 | Edoga et al. |
| 7,364,060 B2 | 4/2008 | Milliman |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,404,508 B2 | 7/2008 | Smith et al. |
| 7,407,075 B2 | 8/2008 | Holsten et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| 7,419,080 B2 | 9/2008 | Smith et al. |
| 7,422,137 B2 | 9/2008 | Manzo |
| 7,422,138 B2 | 9/2008 | Bilotti et al. |
| 7,422,139 B2 | 9/2008 | Shelton, IV et al. |
| 7,431,189 B2 | 10/2008 | Shelton, IV et al. |
| 7,431,191 B2 | 10/2008 | Milliman |
| 7,438,718 B2 | 10/2008 | Milliman et al. |
| 7,441,684 B2 | 10/2008 | Shelton, IV et al. |
| 7,448,525 B2 | 11/2008 | Shelton, IV et al. |
| 7,455,676 B2 | 11/2008 | Holsten et al. |
| 7,455,682 B2 | 11/2008 | Viola |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,546,939 B2 | 6/2009 | Adams et al. |
| 7,546,940 B2 | 6/2009 | Milliman et al. |
| 7,547,312 B2 | 6/2009 | Bauman et al. |
| 7,549,564 B2 | 6/2009 | Boudreaux |
| 7,556,186 B2 | 7/2009 | Milliman |
| 7,559,451 B2 | 7/2009 | Sharma et al. |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,585,306 B2 | 9/2009 | Abbott et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,600,663 B2 | 10/2009 | Green |
| 7,611,038 B2 | 11/2009 | Racenet et al. |
| 7,635,385 B2 | 12/2009 | Milliman et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,686,201 B2 | 3/2010 | Csiky |
| 7,694,864 B2 | 4/2010 | Okada |
| 7,699,204 B2 | 4/2010 | Viola |
| 7,699,835 B2 | 4/2010 | Lee et al. |
| 7,708,181 B2 | 5/2010 | Cole et al. |
| 7,717,313 B2 | 5/2010 | Criscuolo et al. |
| 7,721,931 B2 | 5/2010 | Shelton, IV et al. |
| 7,721,932 B2 | 5/2010 | Cole et al. |
| 7,726,539 B2 | 6/2010 | Holsten et al. |
| 7,738,971 B2 | 6/2010 | Swayze |
| 7,740,159 B2 | 6/2010 | Shelton, IV et al. |
| 7,743,958 B2 | 6/2010 | Orban, III |
| 7,743,960 B2 | 6/2010 | Whitman et al. |
| 7,744,627 B2 | 6/2010 | Orban, III et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,812 B2 | 9/2010 | Moore et al. |
| 7,793,813 B2 | 9/2010 | Bettuchi |
| 7,799,039 B2 | 9/2010 | Shelton, IV et al. |
| 7,802,712 B2 | 9/2010 | Milliman et al. |
| 7,822,458 B2 | 10/2010 | Webster, III et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,534 B2 | 12/2010 | Viola et al. |
| 7,845,536 B2 | 12/2010 | Viola et al. |
| 7,845,537 B2 | 12/2010 | Shelton, IV et al. |
| 7,845,538 B2 | 12/2010 | Whitman |
| 7,857,185 B2 | 12/2010 | Swayze |
| 7,857,187 B2 | 12/2010 | Milliman |

(56) References Cited

U.S. PATENT DOCUMENTS

| | | |
|---|---|---|
| 7,870,989 B2 | 1/2011 | Viola et al. |
| 7,886,951 B2 | 2/2011 | Hessler |
| 7,896,215 B2 | 3/2011 | Adams et al. |
| 7,900,805 B2 | 3/2011 | Shelton, IV et al. |
| 7,900,806 B2 | 3/2011 | Chen et al. |
| 7,905,897 B2 | 3/2011 | Whitman et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,230 B2 | 4/2011 | Whitman et al. |
| 7,918,377 B2 | 4/2011 | Measamer et al. |
| 7,922,061 B2 | 4/2011 | Shelton, IV et al. |
| 7,922,062 B2 | 4/2011 | Cole et al. |
| 7,922,719 B2 | 4/2011 | Ralph et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,947,034 B2 | 5/2011 | Whitman |
| 7,951,071 B2 | 5/2011 | Whitman et al. |
| 7,951,166 B2 | 5/2011 | Orban, III et al. |
| 7,954,682 B2 | 6/2011 | Giordano et al. |
| 7,959,050 B2 | 6/2011 | Smith et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,967,181 B2 | 6/2011 | Viola et al. |
| 7,975,895 B2 | 7/2011 | Milliman |
| 7,992,758 B2 | 8/2011 | Whitman et al. |
| 8,002,795 B2 | 8/2011 | Beetel |
| 8,006,701 B2 | 8/2011 | Bilotti et al. |
| 8,006,889 B2 | 8/2011 | Adams et al. |
| 8,011,550 B2 | 9/2011 | Aranyi et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,178 B2 | 9/2011 | Colson et al. |
| 8,016,855 B2 | 9/2011 | Whitman et al. |
| 8,016,858 B2 | 9/2011 | Whitman |
| 8,020,741 B2 | 9/2011 | Cole et al. |
| 8,020,743 B2 | 9/2011 | Shelton, IV |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,052,024 B2 | 11/2011 | Viola et al. |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,406 B2 | 2/2012 | Holsten et al. |
| 8,113,407 B2 | 2/2012 | Holsten et al. |
| 8,114,118 B2 | 2/2012 | Knodel et al. |
| 8,123,103 B2 | 2/2012 | Milliman |
| 8,127,975 B2 | 3/2012 | Olson et al. |
| 8,128,645 B2 | 3/2012 | Sonnenschein et al. |
| 8,132,703 B2 | 3/2012 | Milliman et al. |
| 8,132,705 B2 | 3/2012 | Viola et al. |
| 8,136,712 B2 | 3/2012 | Zingman |
| 8,146,790 B2 | 4/2012 | Milliman |
| 8,146,791 B2 | 4/2012 | Bettuchi et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,181,838 B2 | 5/2012 | Milliman et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,220,367 B2 | 7/2012 | Hsu |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,235,273 B2 | 8/2012 | Olson et al. |
| 8,241,322 B2 | 8/2012 | Whitman et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,272,554 B2 | 9/2012 | Whitman et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,292,150 B2 | 10/2012 | Bryant |
| 8,292,888 B2 | 10/2012 | Whitman |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,342,379 B2 | 1/2013 | Whitman et al. |
| 8,343,185 B2 | 1/2013 | Milliman et al. |
| 8,348,130 B2 | 1/2013 | Shah et al. |
| 8,348,855 B2 | 1/2013 | Hillely et al. |
| 8,353,438 B2 | 1/2013 | Baxter, III et al. |
| 8,353,439 B2 | 1/2013 | Baxter, III et al. |
| 8,353,440 B2 | 1/2013 | Whitman et al. |
| 8,353,930 B2 | 1/2013 | Heinrich et al. |
| 8,357,144 B2 | 1/2013 | Whitman et al. |
| 8,360,295 B2 | 1/2013 | Milliman et al. |
| 8,365,633 B2 | 2/2013 | Simaan et al. |
| 8,365,972 B2 | 2/2013 | Aranyi et al. |
| 8,365,974 B2 | 2/2013 | Milliman |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,904 B2 | 4/2013 | Wenchell et al. |
| 8,418,905 B2 | 4/2013 | Milliman |
| 8,418,909 B2 | 4/2013 | Kostrzewski |
| 8,424,535 B2 | 4/2013 | Hessler et al. |
| 8,424,739 B2 | 4/2013 | Racenet et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,454,585 B2 | 6/2013 | Whitman |
| 8,485,414 B2 | 7/2013 | Criscuolo et al. |
| 8,490,853 B2 | 7/2013 | Criscuolo et al. |
| 8,505,802 B2 | 8/2013 | Viola et al. |
| 8,511,533 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,551,138 B2 | 10/2013 | Orban, III et al. |
| 8,561,871 B2 | 10/2013 | Rajappa et al. |
| 8,561,874 B2 | 10/2013 | Scirica |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,602,287 B2 | 12/2013 | Yates et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |

(56) References Cited

U.S. PATENT DOCUMENTS

| | | |
|---|---|---|
| 8,623,000 B2 | 1/2014 | Humayun et al. |
| 8,627,995 B2 | 1/2014 | Smith et al. |
| 8,631,993 B2 | 1/2014 | Kostrzewski |
| 8,632,463 B2 | 1/2014 | Drinan et al. |
| 8,636,187 B2 | 1/2014 | Hueil et al. |
| 8,636,766 B2 | 1/2014 | Milliman et al. |
| 8,640,940 B2 | 2/2014 | Ohdaira |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,662,370 B2 | 3/2014 | Takei |
| 8,663,258 B2 | 3/2014 | Bettuchi et al. |
| 8,672,206 B2 | 3/2014 | Aranyi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,733,611 B2 | 5/2014 | Milliman |
| 8,758,391 B2 | 6/2014 | Swayze et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,851,355 B2 | 10/2014 | Aranyi et al. |
| 8,858,571 B2 | 10/2014 | Shelton, IV et al. |
| 8,888,762 B2 | 11/2014 | Whitman |
| 8,899,462 B2 | 12/2014 | Kostrzewski et al. |
| 8,905,289 B2 | 12/2014 | Patel et al. |
| 8,919,630 B2 | 12/2014 | Milliman |
| 8,931,680 B2 | 1/2015 | Milliman |
| 8,950,646 B2 | 2/2015 | Viola |
| 8,960,519 B2 | 2/2015 | Whitman et al. |
| 8,967,443 B2 | 3/2015 | McCuen |
| 8,968,276 B2 | 3/2015 | Zemlok et al. |
| 9,016,545 B2 | 4/2015 | Aranyi et al. |
| 9,023,014 B2 | 5/2015 | Chowaniec et al. |
| 9,033,868 B2 | 5/2015 | Whitman et al. |
| 9,055,943 B2 | 6/2015 | Zemlok et al. |
| 9,072,515 B2 | 7/2015 | Hall et al. |
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,899 B2 | 8/2015 | Garrison et al. |
| 2001/0031975 A1 | 10/2001 | Whitman et al. |
| 2003/0038938 A1 | 2/2003 | Jung et al. |
| 2003/0111507 A1 | 6/2003 | Nunez |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |
| 2005/0051597 A1 | 3/2005 | Toledano |
| 2005/0107813 A1 | 5/2005 | Gilete Garcia |
| 2005/0125027 A1 | 6/2005 | Knodel et al. |
| 2005/0131442 A1 | 6/2005 | Yachia et al. |
| 2006/0000869 A1 | 1/2006 | Fontayne |
| 2006/0011698 A1 | 1/2006 | Okada et al. |
| 2006/0142656 A1 | 6/2006 | Malackowski et al. |
| 2006/0142744 A1 | 6/2006 | Boutoussov |
| 2006/0201989 A1 | 9/2006 | Ojeda |
| 2006/0259073 A1 | 11/2006 | Miyamoto et al. |
| 2006/0278680 A1 | 12/2006 | Viola et al. |
| 2006/0284730 A1 | 12/2006 | Schmid et al. |
| 2007/0023477 A1 | 2/2007 | Whitman et al. |
| 2007/0027473 A1 | 2/2007 | Vresh et al. |
| 2007/0029363 A1 | 2/2007 | Popov |
| 2007/0060952 A1 | 3/2007 | Roby et al. |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2009/0012533 A1 | 1/2009 | Barbagli et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209990 A1 | 8/2009 | Yates et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2009/0254094 A1 | 10/2009 | Knapp et al. |
| 2009/0299141 A1 | 12/2009 | Downey et al. |
| 2010/0019016 A1 | 1/2010 | Edoga et al. |
| 2010/0023022 A1 | 1/2010 | Zeiner et al. |
| 2010/0051668 A1 | 3/2010 | Milliman et al. |
| 2010/0069942 A1 | 3/2010 | Shelton, IV |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0225073 A1 | 9/2010 | Porter et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0077673 A1 | 3/2011 | Grubac et al. |
| 2011/0114697 A1 | 5/2011 | Baxter, III et al. |
| 2011/0114700 A1 | 5/2011 | Baxter, III et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0144640 A1 | 6/2011 | Heinrich et al. |
| 2011/0147432 A1 | 6/2011 | Heinrich et al. |
| 2011/0155783 A1 | 6/2011 | Rajappa et al. |
| 2011/0174099 A1 | 7/2011 | Ross et al. |
| 2011/0184245 A1 | 7/2011 | Xia et al. |
| 2011/0192882 A1 | 8/2011 | Hess et al. |
| 2011/0204119 A1 | 8/2011 | McCuen |
| 2011/0218522 A1 | 9/2011 | Whitman |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0089131 A1 | 4/2012 | Zemlok et al. |
| 2012/0143002 A1 | 6/2012 | Aranyi et al. |
| 2012/0145755 A1 | 6/2012 | Kahn |
| 2012/0172924 A1 | 7/2012 | Allen, IV |
| 2012/0193395 A1 | 8/2012 | Pastorelli et al. |
| 2012/0193398 A1 | 8/2012 | Williams et al. |
| 2012/0223121 A1 | 9/2012 | Viola et al. |
| 2012/0232339 A1 | 9/2012 | Csiky |
| 2012/0253329 A1 | 10/2012 | Zemlok et al. |
| 2012/0273548 A1 | 11/2012 | Ma et al. |
| 2012/0310220 A1 | 12/2012 | Malkowski et al. |
| 2012/0323226 A1 | 12/2012 | Chowaniec et al. |
| 2012/0325888 A1 | 12/2012 | Qiao et al. |

(56) References Cited

U.S. PATENT DOCUMENTS

| | | |
|---|---|---|
| 2013/0015232 A1 | 1/2013 | Smith et al. |
| 2013/0018361 A1 | 1/2013 | Bryant |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214025 A1 | 8/2013 | Zemlok et al. |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0274722 A1 | 10/2013 | Kostrzewski et al. |
| 2013/0277411 A1 | 10/2013 | Hodgkinson et al. |
| 2013/0277412 A1 | 10/2013 | Gresham et al. |
| 2013/0282052 A1 | 10/2013 | Aranyi et al. |
| 2013/0284792 A1 | 10/2013 | Ma |
| 2013/0292449 A1 | 11/2013 | Bettuchi et al. |
| 2013/0292451 A1 | 11/2013 | Viola et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0008413 A1 | 1/2014 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0012317 A1 | 1/2014 | Orban et al. |
| 2014/0025046 A1 | 1/2014 | Williams et al. |
| 2014/0110455 A1 | 4/2014 | Ingmanson et al. |
| 2014/0166728 A1 | 6/2014 | Swayze et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236173 A1 | 8/2014 | Scirica et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2015/0014392 A1 | 1/2015 | Williams et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0133957 A1 | 5/2015 | Kostrzewski |
| 2015/0150547 A1 | 6/2015 | Ingmanson et al. |
| 2015/0150574 A1 | 6/2015 | Richard et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0201931 A1 | 7/2015 | Zergiebel et al. |
| 2016/0361057 A1* | 12/2016 | Williams ............ A61B 17/068 |

FOREIGN PATENT DOCUMENTS

| | | |
|---|---|---|
| CA | 2824590 A1 | 4/2014 |
| CN | 102247182 A | 11/2011 |
| DE | 1057729 B | 5/1959 |
| DE | 3301713 A1 | 7/1984 |
| DE | 102008053842 A1 | 5/2010 |
| EP | 0152382 A2 | 8/1985 |
| EP | 0173451 A1 | 3/1986 |
| EP | 0282157 A1 | 3/1986 |
| EP | 0190022 A2 | 8/1986 |
| EP | 0503689 A2 | 9/1992 |
| EP | 0705571 A1 | 4/1996 |
| EP | 1354560 A2 | 10/2003 |
| EP | 1769754 A1 | 4/2007 |
| EP | 2055243 A2 | 5/2009 |
| EP | 2316345 A1 | 5/2011 |
| EP | 2333509 A1 | 6/2011 |
| EP | 2524656 A2 | 11/2012 |
| EP | 2524658 A1 | 11/2012 |
| EP | 3078335 A1 | 10/2016 |
| EP | 3146905 A1 | 3/2017 |
| EP | 3412226 A1 | 12/2018 |
| ES | 2333509 A1 | 2/2010 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 08038488 | 2/1996 |
| JP | 2005125075 A | 5/2005 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 0154594 A1 | 8/2001 |
| WO | 2008107918 A1 | 9/2008 |
| WO | 2011108840 A2 | 9/2011 |
| WO | 2012/040984 A1 | 4/2012 |

OTHER PUBLICATIONS

European Search Report dated Mar. 1, 2021, corresponding to counterpart European Application No. 20183904.0; 11 pages.

* cited by examiner

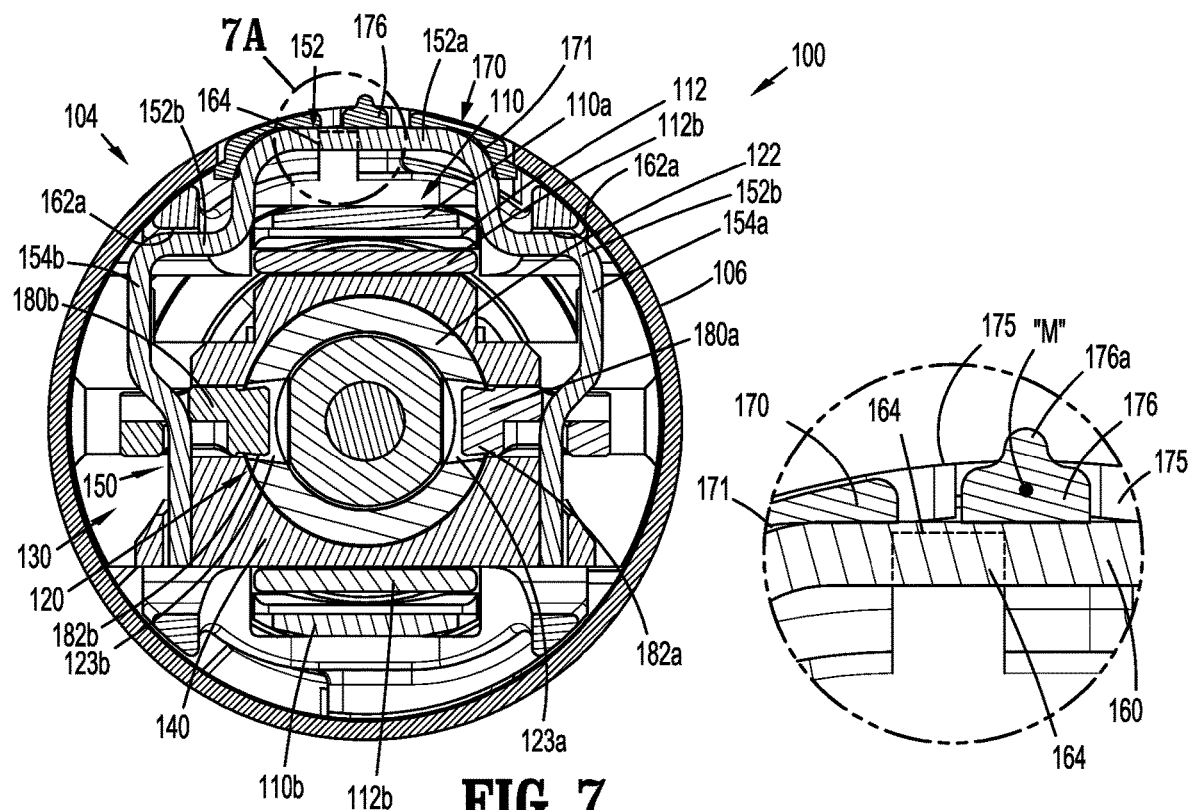
FIG. 7
FIG. 7A
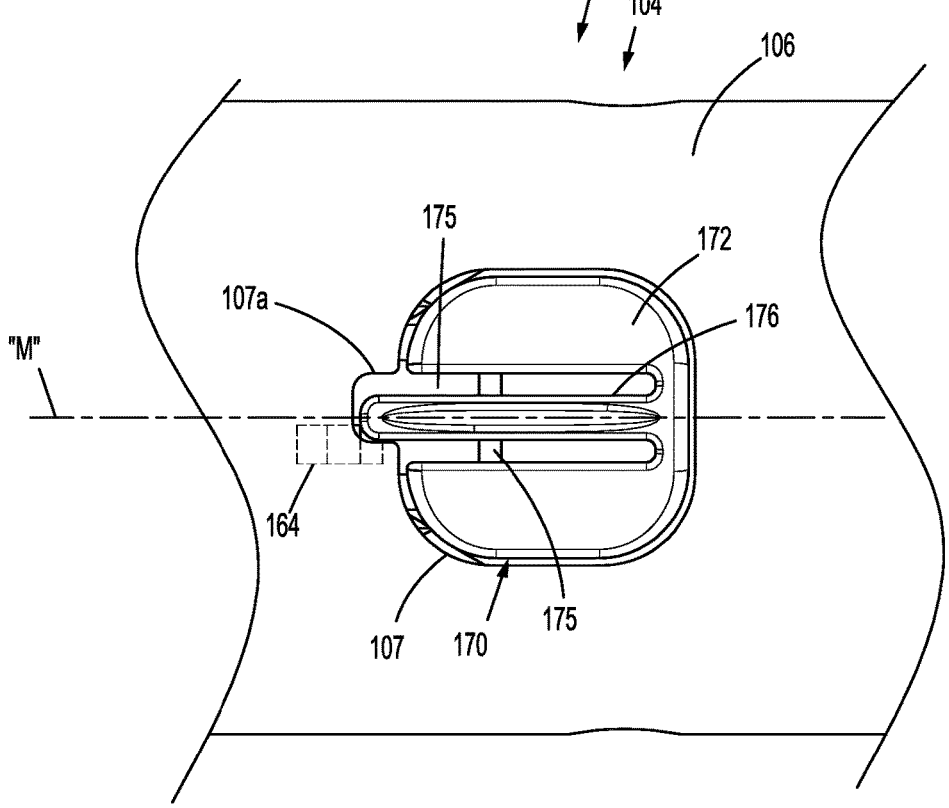
FIG. 8

RETAINING MECHANISMS FOR TROCAR ASSEMBLIES

FIELD

The disclosure relates to reusable adapter assemblies for surgical stapling devices. More particularly, the disclosure relates to retaining mechanisms for releasably securing removable trocar assemblies within reusable adapter assemblies.

BACKGROUND

Surgical devices for applying staples, clips, or other fasteners to tissue are well known. Typically, endoscopic stapling devices include an actuation unit, i.e., a handle assembly for actuating the device, a shaft for endoscopic access to a body cavity, and a tool assembly disposed at a distal end of the shaft. In certain of these devices, the shaft includes an adapter assembly having a proximal end securable to the handle assembly and a distal end securable to the tool assembly.

Circular stapling devices typically include a trocar assembly for supporting and positioning an attached anvil assembly in relation to a staple cartridge of the tool assembly. The trocar assembly may be releasably securable within the adapter assembly to permit cleaning, sterilizing, and reuse of the adapter assembly. It would be beneficial to have a retaining mechanism for releasably securing the trocar assembly to the adapter assembly.

SUMMARY

An adapter assembly for connecting a loading unit to a handle assembly includes an outer sleeve, a trocar assembly releasably securable within the outer sleeve, and a retaining mechanism configured to releasably secure the trocar assembly within the outer sleeve. The trocar assembly includes a trocar housing defining first and second openings. The retaining mechanism includes a retaining block, a cam wire moveably positioned relative to the retaining block between a lock position and a release position, a retaining block extension configured to maintain the cam wire relative to the retaining block, a button member in operable engagement with the cam wire, and a pair of retaining members moveable from a first position received within the first and second openings of the trocar assembly when the cam wire is in the lock position and a second position spaced from the trocar assembly when the cam wire is in the release position. The retaining block extension includes a stop tab. The button member includes a center beam moveable from an unflexed position in engagement with the stop tab of the retaining block extension to prevent movement of the button member to a flexed position out of alignment with the stop tab to permit movement of the button member.

In embodiments, the button member is pivotable relative to the retaining block from a non-depressed position when the center beam is in the unflexed position and a depressed position when the center beam is in the flexed position. Depression of the button member may cause the cam wire to move from the lock position to the release position.

The center beam may include a rib configured for operable engagement by a user. The button member may define a relief on either side of the center beam to permit movement of the center beam between the unflexed and flexed positions. The button member may define a midline. The stop member may be aligned with the midline. The center beam may be aligned with the midline when in the unflexed position and is misaligned with the midline when in the flexed position. The retaining block may define a central opening for receiving the trocar assembly. Each of the first and second retaining members may include a wedge-shaped free end.

Another adapter assembly for connecting a loading unit to a handle assembly includes an outer sleeve, a trocar assembly releasably securable within the outer sleeve, and a retaining mechanism configured to releasably secure the trocar assembly within the outer sleeve. The trocar assembly includes a trocar housing defining first and second openings. The retaining mechanism includes a retaining block, a cam wire moveably positioned relative to the retaining block between a lock position and a release position, an upper retaining block extension configured to maintain the cam wire relative to the retaining, a button member for moving the cam wire between the lock and release positions, a pair of retaining members moveable from a first position received within the first and second openings of the trocar assembly when the cam wire is in the lock position and a second position spaced from the trocar assembly when the cam wire is in the release position, a lower retaining block extension disposed opposite the upper retaining block extension, and a sliding button moveable between a first position in engagement with the cam wire to a second position spaced from the cam wire. Movement of the sliding button member relative to the lower retaining block permits movement of the cam wire from the lock position to the release position.

In embodiments, the cam wire includes first and second free ends and the sliding button member includes first and second stop members configured to engage the free ends of the cam wire to prevent movement of the cam wire to the release position. The sliding button member may be biased to the first position by a biasing member. The biasing member may be a coil spring. The sliding button member may be configured for operable engagement by a user. The button member may be pivotable relative to the upper retaining block extension.

The adapter assembly may include a collar assembly received about the outer sleeve. Movement of the collar assembly from a first position to a second positon moves the button member from the non-depressed position to the depressed position. The collar assembly may move proximally from the first position to the second position. Alternatively, the collar assembly is rotated about the outer sleeve when moved from the first position to the second position. The collar assembly may be biased to the first position by a coil spring. The outer sleeve may include a pin for engagement with the collar assembly to limit movement of the collar assembly.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein:

FIG. 7 is a cross-sectional end view the adapter assembly shown in FIG. 2 taken along line 7-7 shown in FIG. 3, with the retainer mechanism in a lock position;

FIG. 8 is a top view of a portion of the adapter assembly including a button member of the retainer mechanism shown in FIG. 5, with a center beam in a first or unflexed condition;

DETAILED DESCRIPTION

Figure 1:
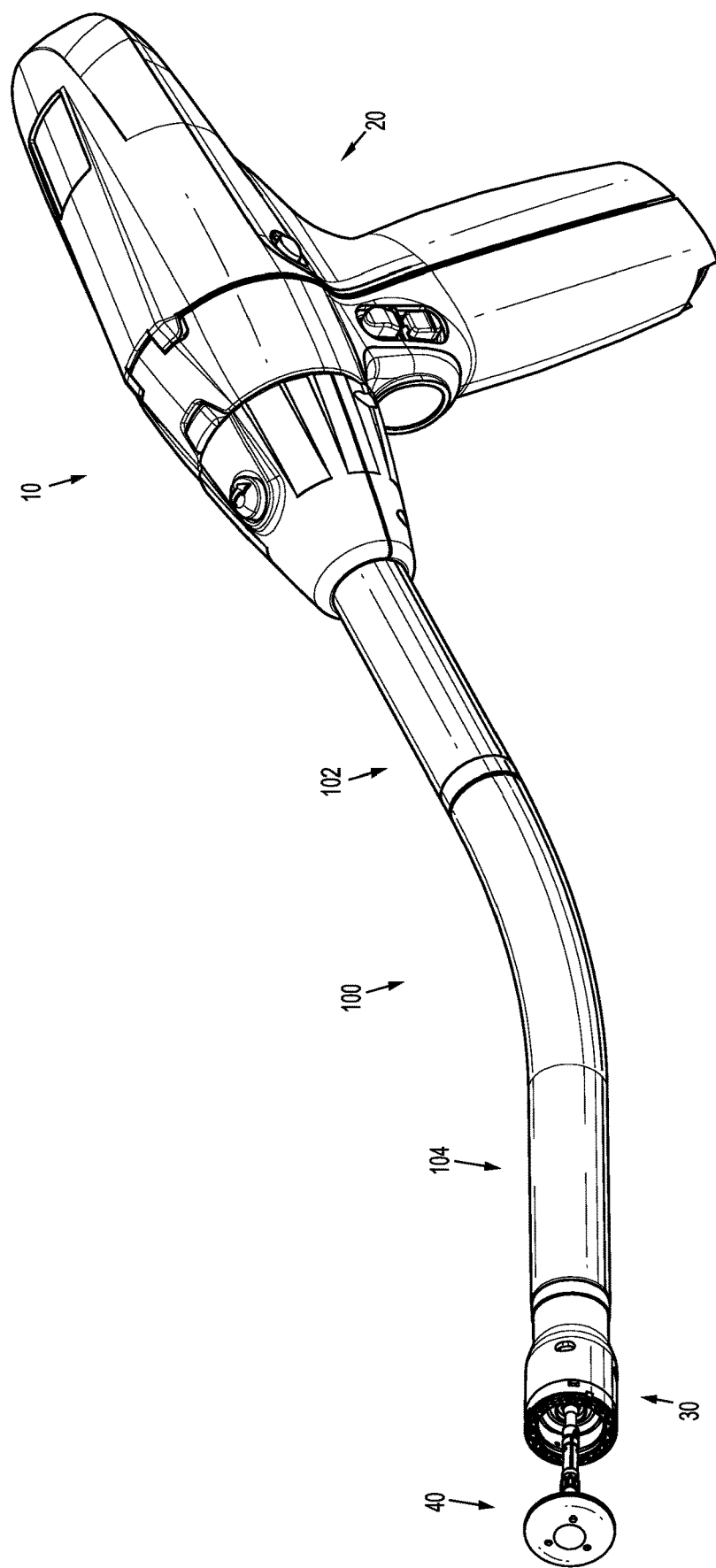
FIG. 1 is a perspective view of a surgical stapling device including an handle assembly and an adapter assembly according to an exemplary embodiment of the disclosure.

Embodiments of the disclosed adapter assembly including a retaining mechanism for securing a removable trocar assembly therein will now be described in detail with reference to the drawings in which like reference numerals designate identical or corresponding elements in each of the several views. As is common in the art, the term "proximal" refers to that part or component closer to the user or operator, i.e. surgeon or clinician, while the term "distal" refers to that part or component further away from the user.

Figure 2:
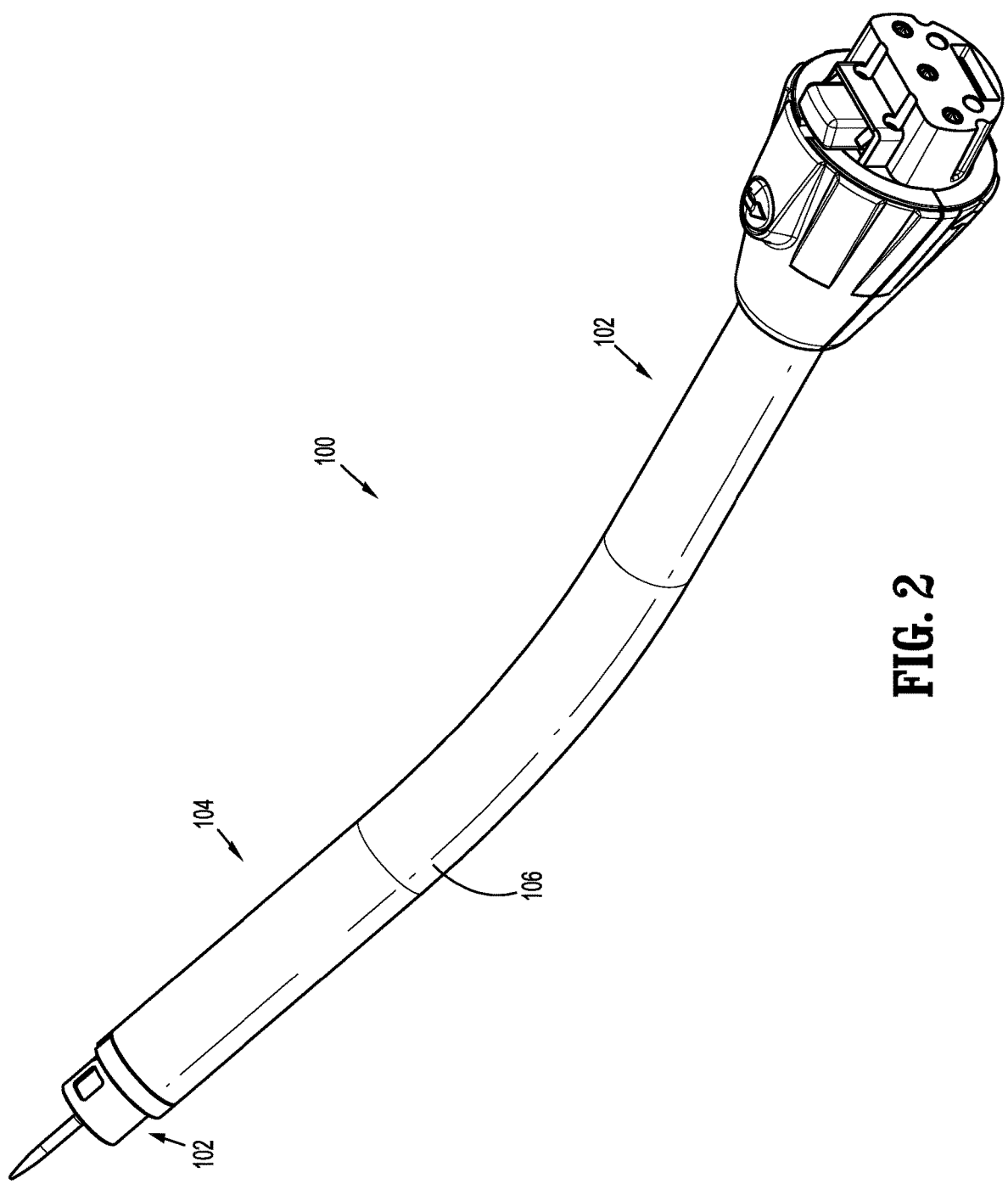
FIG. 2 is a perspective view of the adapter assembly shown in FIG. 1 with a removable trocar assembly extending from a distal portion of the adapter assembly.

Referring initially to FIG. 1, an adapter assembly according to an embodiment of the disclosure, shown generally as adapter assembly 100, is a component of a surgical stapling device 10. The surgical stapling device 10 further includes a powered handle assembly 20 for actuating a loading unit 30, and an anvil assembly 40 supported relative to the loading unit 30. The loading unit 30 and the anvil assembly 40 form a tool assembly of the surgical stapling device 10. Although shown and described with reference to surgical stapling device 10, aspects of the disclosure may be modified for use with manual surgical stapling devices having various configurations, and with powered surgical stapling devices having alternative configurations. For a detailed description of exemplary surgical stapling devices, please refer to U.S. Pat. Nos. 9,023,014 and 9,055,943. With reference to FIG. 2, the adapter assembly 100 includes a proximal portion 102 configured for operable connection to the handle assembly 20 (FIG. 1) and a distal portion 104 configured for operable connection to the loading unit 30 (FIG. 1) and to the anvil assembly 40 (FIG. 1). Although shown and described as forming an integral unit, it is envisioned that the proximal and distal portions 102, 104 may be formed as separate units that are releasably securable to one another.

The adapter assembly 100 will only be described to the extent necessary to fully disclose the aspects of the disclosure. For a detailed description of an exemplary adapter assembly, please refer to U.S. Pat. No. 10,226,254 ("the '254 patent").

Figure 3:
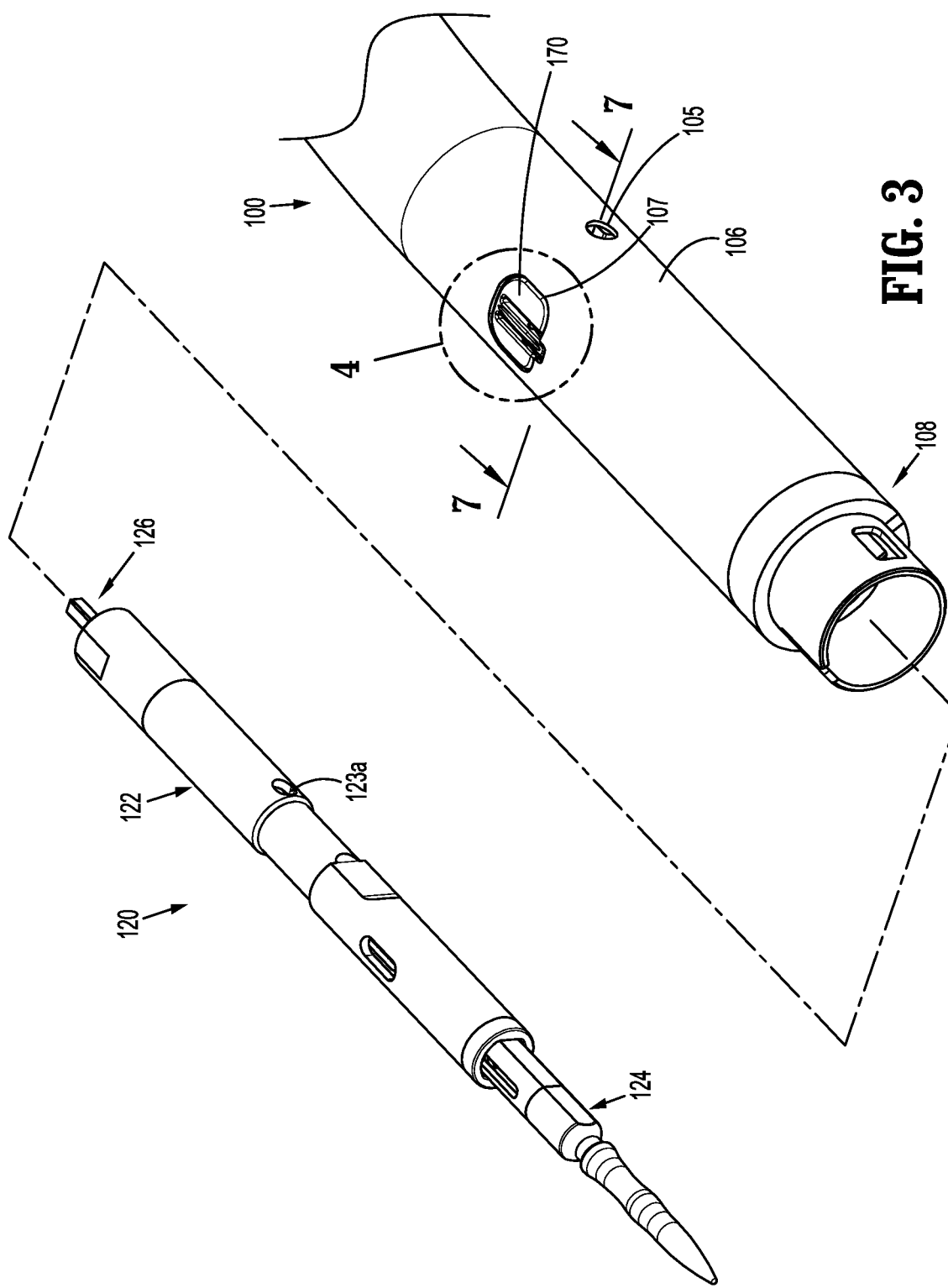
FIG. 3 is a perspective view of the distal portion of the adapter assembly and the removable trocar assembly shown in FIG. 1, with the removable trocar removed from within the adapter assembly.
Figure 4:
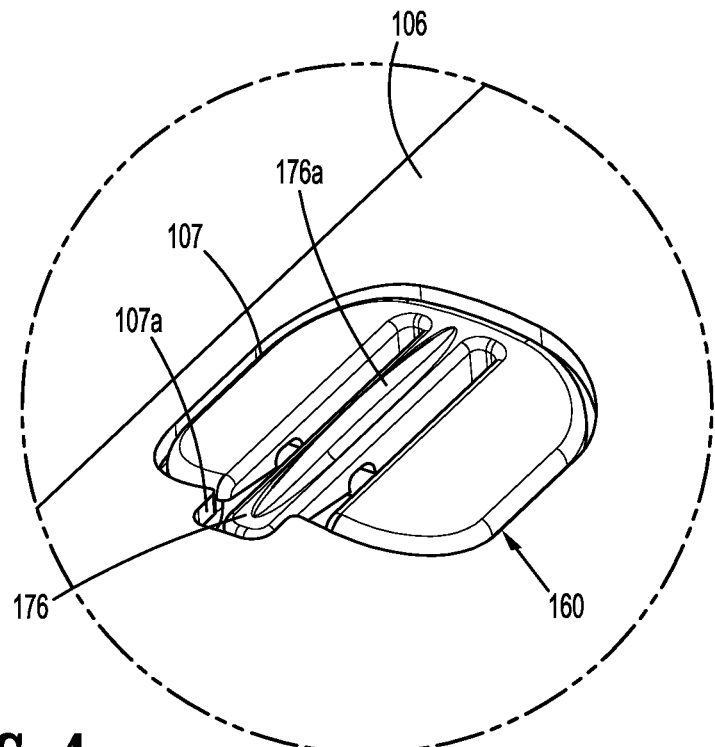
FIG. 4 is an exploded view of the indicated area of detail shown in FIG. 3.

With additional reference to FIGS. 3 and 4, the adapter assembly 100 includes an outer sleeve 106, and a connector housing 108 secured to a distal end of the outer sleeve 106. The connector housing 108 is configured to releasably secure a loading unit, e.g., the loading unit 30 (FIG. 1), to the adapter assembly 100. The outer sleeve 106 defines a flush port 105 (FIG. 3) and an opening 107 through which a button member 170 of a trocar retaining mechanism 130 is operably disposed. As will be described in further detail below, the outer sleeve 106 further includes an asymmetric cutout 107a (FIG. 4) in communication with the opening 107.

Figure 5:
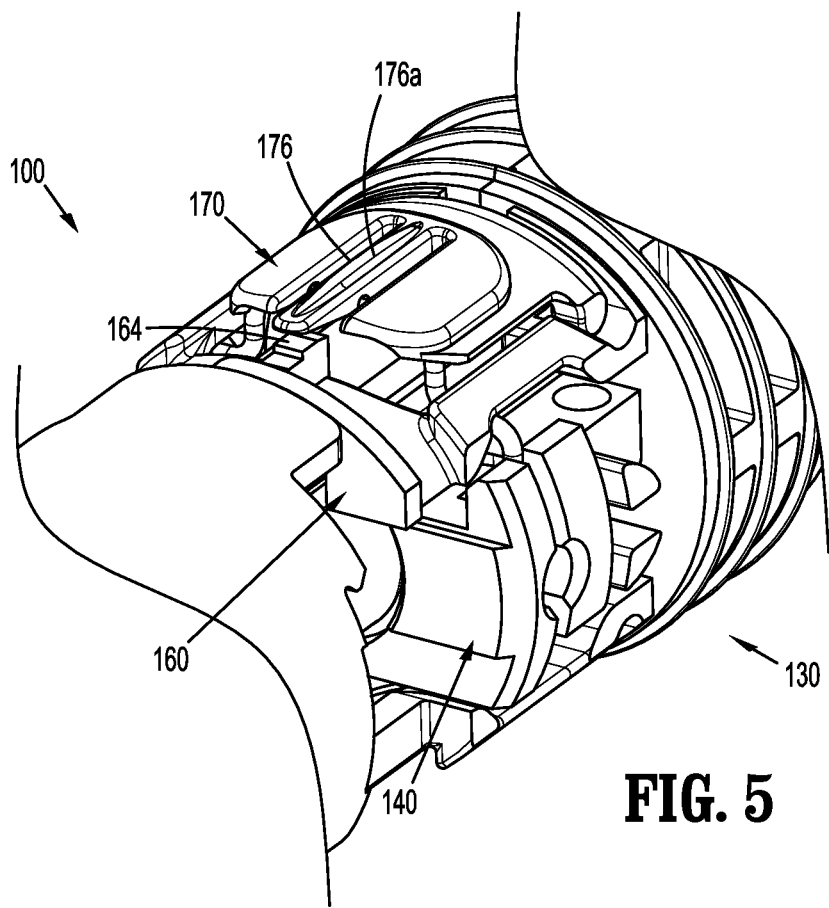
FIG. 5 is a perspective view of the distal portion of the adapter assembly shown in FIG. 2, with an outer sleeve removed to expose a retaining mechanism.

With additional reference to FIG. 5, the adapter assembly 100 further includes a trocar assembly 120 (FIG. 3), and a retaining mechanism 130 releasably securing the trocar assembly 120 relative to the outer sleeve 106 (FIG. 3) of the adapter assembly 100. The trocar assembly 120 will only be described to the extent necessary to fully describe the aspects of the disclosure. For a detailed description of the structure and function of an exemplary trocar assembly, please refer to the '254 patent. With particular reference to FIG. 3, the trocar assembly 120 of the adapter assembly 100 (FIG. 2) includes a trocar housing 122, a trocar member 124 slidably disposed within the trocar housing 122, and a drive screw 126 operably received within the trocar member 124 for axially moving the trocar member 124 relative to the trocar housing 122. The trocar housing 122 defines first and second locking openings 123a, 123b (FIG. 7) for receiving respective locking portions 182a, 182b of first and second retainer members 180a, 180b (FIG. 6) of a retaining mechanism 130 of the adapter assembly 100.

Turning briefly to FIG. 7, the retaining mechanism 130 of the adapter assembly 100 is disposed between first and second drive members 110a, 110b, 112a, 112b of respective inner and outer drive assemblies 110, 112. The first and second drive assemblies 110, 112 are operably connected to first and second drive shafts (not shown) in a proximal portion 102 of the adapter assembly 100 for effecting operation of a loading unit, e.g., the loading unit 30 (FIG. 1), to perform first and second functions. More particularly, the first and second drive members 110a, 110b, 112a, 112b of the respective first and second drive assemblies 110, 112 are configured for longitudinal movement within the distal portion 104 of the adapter assembly 100. In embodiments, advancement of the first drive assembly 110 effects tissue stapling, and advancement of the second drive assembly 112 effects tissue cutting.

Figure 6:
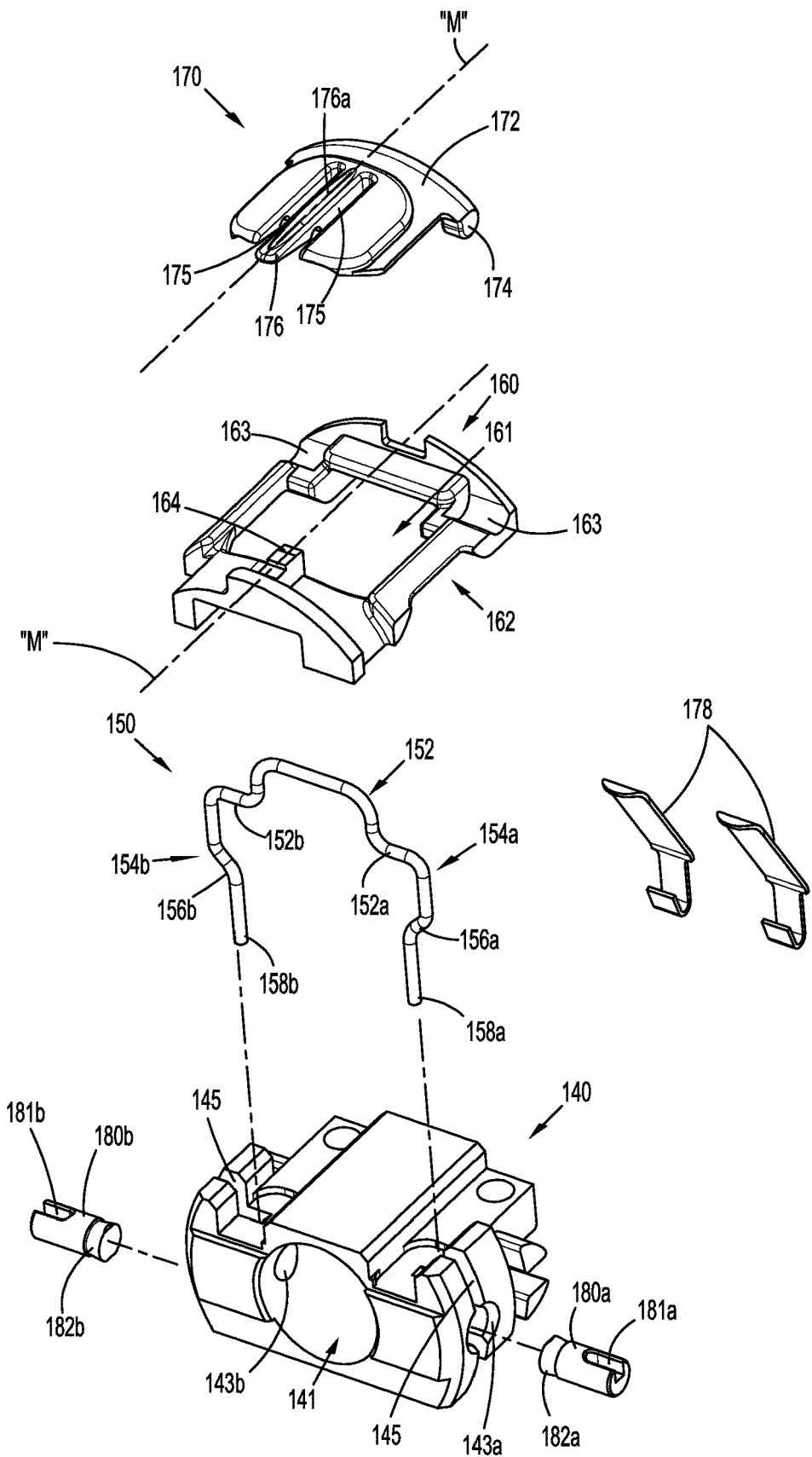
FIG. 6 is a side perspective view of the retaining mechanism shown in FIG. 5, with components separated.

The first and second drive assemblies 110, 112 will only be described to the extent necessary to fully disclose the aspects of the disclosure. For a detailed description of exemplary drive assemblies, please refer to the '254 patent. With reference now to FIGS. 5 and 6, the retaining mechanism 130 of the adapter assembly 100 includes a retaining block 140, a cam wire 150 (FIG. 6) supported by the retaining block 140, a retaining block extension 160 for maintaining the cam wire 150 relative to the retaining block 140, a button member 170 in operable engagement with the cam wire 150 and pivotally supported relative to the retaining block 140, and first and second retainer members 180a, 180b (FIG. 6) supported by the cam wire 150 within the retaining block 140.

With particular reference to FIG. 6, the retaining block 140 of the retaining mechanism 130 defines a central opening 141 for receiving the trocar assembly 120 (FIG. 3), first and second opposed cylindrical openings 143a, 143b in communication with the central opening 141 for receiving the respective first and second retainer members 180a, 180b, and a channel or slot 145 extending about a perimeter of the retaining block 140 and through the first and second cylindrical openings 143a, 143b in the retaining block 140 for receiving the cam wire 150. The first and second retainer members 180a, 180b of the retaining mechanism 130 are supported within the first and second cylindrical openings 143a, 143b of the retaining block 140 by the cam wire 150 and are configured to be received within first and second locking openings 123a, 123b of the trocar housing 122 of the trocar assembly 120 when the trocar assembly 120 is fully received within the distal portion 104 (FIG. 2) of the adapter assembly 100.

The cam wire 150 of the retaining mechanism 130 includes a substantially U-shaped member having a backspan 152, and first and second legs 154a, 154b extending from the backspan 152. The backspan 152 includes a button engagement portion 152a and a pair of shoulders portions 152b on either side of the button engagement portion 152a. Each of the first and second legs 154a, 154b includes an opposed angled section 156a, 156b. The cam wire 150 is received within the channel 145 of the retaining block 140. As will be described in further detail below, the cam wire 150 is moveable between a first or lock position (FIG. 8) when the button member 170 is in an initial or non-depressed position, and a second or release position when the button member 170 is depressed.

With continued reference to FIG. 6, the retaining block extension 160 includes a substantially rectangular frame 162 defining an opening 161 and a pair semi-cylindrical recesses 163. First and second pivot portions 174 (only one shown) of the button member 170 are pivotally supported within the semi-cylindrical recesses 163 in the frame 162 and a body portion 172 of the button member is disposed within the opening 161 in the frame 162. The frame 162 includes a pair of stop surfaces 162a (FIG. 7) for engaging the shoulder portions 152b of the backspan 152 of the cam wire 150, and a stop member, e.g., a stop tab 164, along a midline "m" of the frame 162 for inhibiting depression of the button member 170.

The button member 170 of the retaining mechanism 130 of the adapter assembly 100 (FIG. 2) includes the body portion 172 configured for operable engagement by a user, and the pair of pivot portions 174 configured for reception within the pair of semi-cylindrical recesses 163 of the retaining block extension 160. The button member 170 is configured to engage the engagement portion 152a of the backspan 152 of the cam wire 150. In embodiments, the backspan 152 of the cam wire 150 is secured to the button member 170. For example, and as shown, the body portion 172 of the button member 170 defines a cavity 171 (FIG. 7A) in with the engagement portion 152a of the back span 152 is retained through friction fit. Alternatively, the backspan 152 is secured within the cavity 171 with mechanical fasteners, bonding, welding, adhesives, or in any other suitable manner. The retaining mechanism 130 may include a biasing member, e.g., leaf springs 178 (FIG. 6) for biasing the cam wire 150 outwardly to the first position, and/or the button member 170 outwardly to the non-depressed position (FIG. 7).

The button member 170 of the trocar retaining mechanism 130 further includes a center beam 176, and defines a relief 175 on either side of the center beam 176. The center beam 176 includes a rib 176a, or is otherwise configured for engagement by a user. The center beam 176 and reliefs 175 are configured such that the center beam 176 may be flexed away from a midline "M" of the button member 170. More particularly, the center beam 176 of the button member 170 is configured to align with the stop tab 164 of the retaining block extension 160 when the center beam 176 is in an initial or unflexed condition. In this manner, the center beam 176 of the button member 170 prevents the button member 170 from being depressed. As will be described in further detail below, flexing of the center beam 176 away from the midline "M" of the button member 170 moves the center beam 176 out of alignment with the stop tab 164 of the retaining block extension 160, thereby permitting depression of the button member 170. The reliefs 175 in the button member 170 may also facilitate flushing and cleaning of the adapter assembly 100 (FIG. 2)

The first and second retaining members 180a, 180b of the retaining mechanism 130 form substantially cylindrical bodies 182a, 182b and are supported on the angled portions 156a, 156b of the respective first and second legs 154a, 154b of the cam wire 150. In embodiments, the first and second retaining members 180a, 180b form a wedge-shaped configuration to be received within wedge-shaped first and second locking openings 123a, 123b in the trocar housing 122 of the trocar assembly 120. The first and second retaining members 180a, 180b may include an inclined inner surface (not shown) to facilitate receipt of the trocar assembly 120 through the retaining block 140.

The first and second retaining members 180a, 180b each define a stepped opening 181a, 181b through which the respective angled portion 156a, 156b of the cam wire 150 is received. The cam wire 150 and the stepped openings 181a, 181*b* of the respective first and second retaining members 180*a*, 180*b* are configured such that when the cam wire 150 is in the first position, the first and second retaining members 180*a*, 180*b* extend from within the retaining block 140 into the central passage 141. In this manner, when a trocar assembly 120 is fully seated within the distal portion 104 (FIG. 2) of the adapter assembly 100, the first and second retaining members 180*a*, 180*b* are received within the respective first and second locking openings 123*a*, 123*b* (FIG. 7) of the trocar housing 122 of the trocar assembly 120. Conversely, when the cam wire 150 is in the second or release position, the first and second retainer members 180*a*, 180*b* are retracted from within the central opening 141 of the retaining block 140 to permit insertion and/or removal of the trocar assembly 120 from the distal portion 104 of the adapter assembly 100.

With reference now to FIGS. 7 and 8, the retaining mechanism 130 of the adapter assembly 100 is shown in a first or lock configuration, with the trocar assembly 120 securely received within the distal portion 104 of the adapter assembly 100. In the lock configuration, the cam wire 150 of the retaining mechanism 130, which is secured to the button member 170, is biased to the first position by the leaf springs 178 (FIG. 6). In the first position, the shoulder portions 152*b* of the backspan 152 of the cam wire 150 engage the stop surface 162*a* of the retaining block extension 160. As noted above, when the cam wire 150 is in the first position and the trocar assembly 120 is fully seated within the distal portion 104 (FIG. 2) of the adapter assembly 100, the first and second retainer members 180*a*, 180*b* are received within the respective first and second locking openings 123*a*, 123*b* in the trocar housing 122 of the trocar assembly 120.

The center beam 176 of the button member 170 of the retaining mechanism 130 is shown in the first or unflexed position. In the unflexed position, the center beam 176 aligns with the midline "M" of the button member 170. When aligned with the midline "M", the center beam 176 engages the stop tab 164 of the retaining block extension 160 which is also aligned with the midline "M" of the button member 170, thereby preventing the button member 170 from being depressed.

Figure 9:
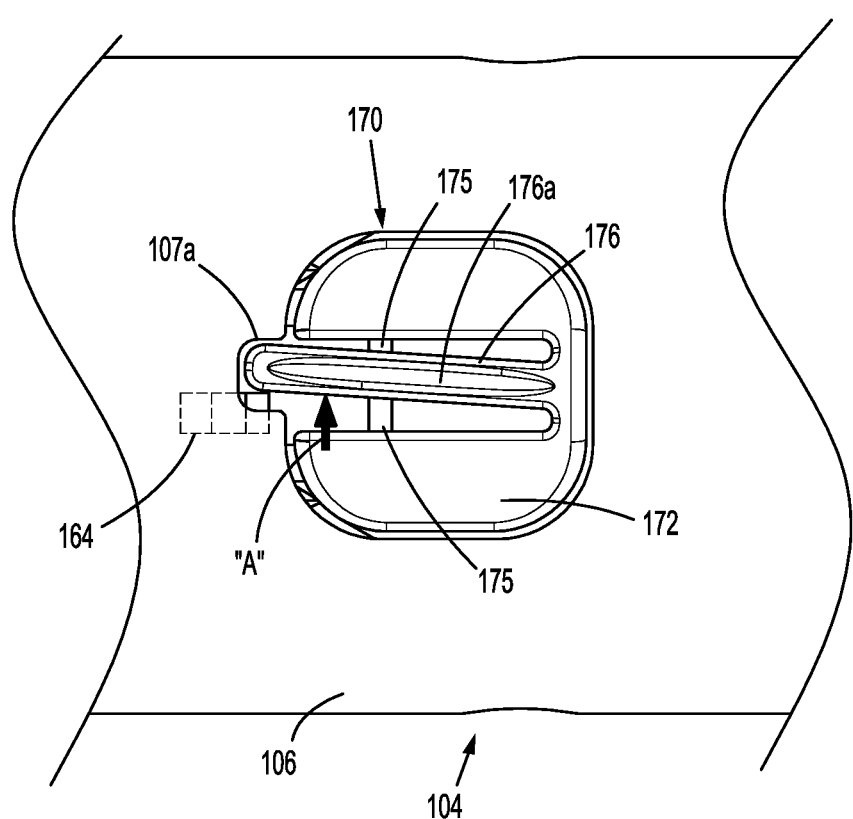
FIG. 9 is the top view shown in FIG. 8 with the center beam of the button member in a second of flexed condition.

Turning to FIG. 9, following use of the adapter assembly 100, or to otherwise remove the trocar assembly 120 from the distal portion 104 of the adapter assembly 100, the rib 176*a* of the center beam 176 of the button member 170 of the retaining mechanism 130 is moved off-center, or away from the midline "M" of the button member 170, to the flexed position, as indicated by arrow "A", to move the center beam 176 of the button member 170 out of alignment with the stop tab 164 of the retaining block extension 160. As noted above, when the center beam 176 of the button member 170 is misaligned with the stop tab 164 of the retaining block extension 160, the stop tab 164 no longer obstructs or inhibits the button member 170 from being depressed.

Figure 10:
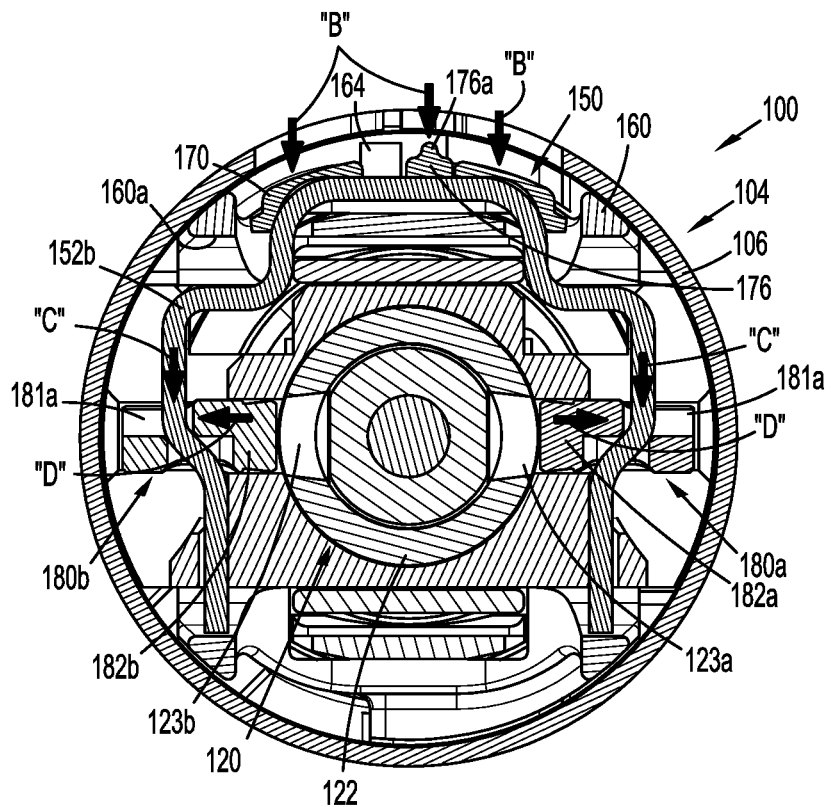
FIG. 10 is the cross-sectional end view of the adapter assembly shown in FIG. 7, with the retainer mechanism in a release position.
Figure 11:
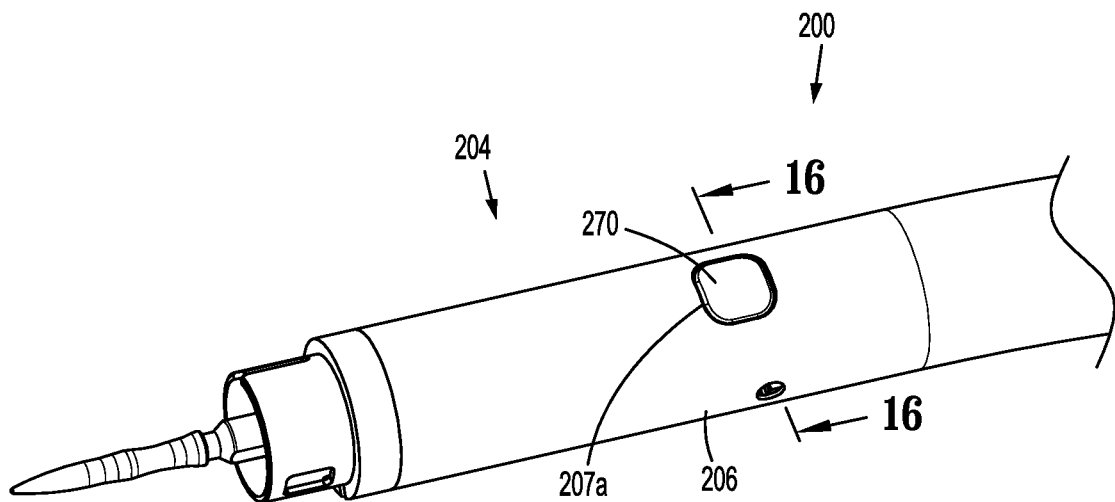
FIG. 11 is a first perspective view of a distal portion of an adapter assembly according to another embodiment of the disclosure.
Figure 12:
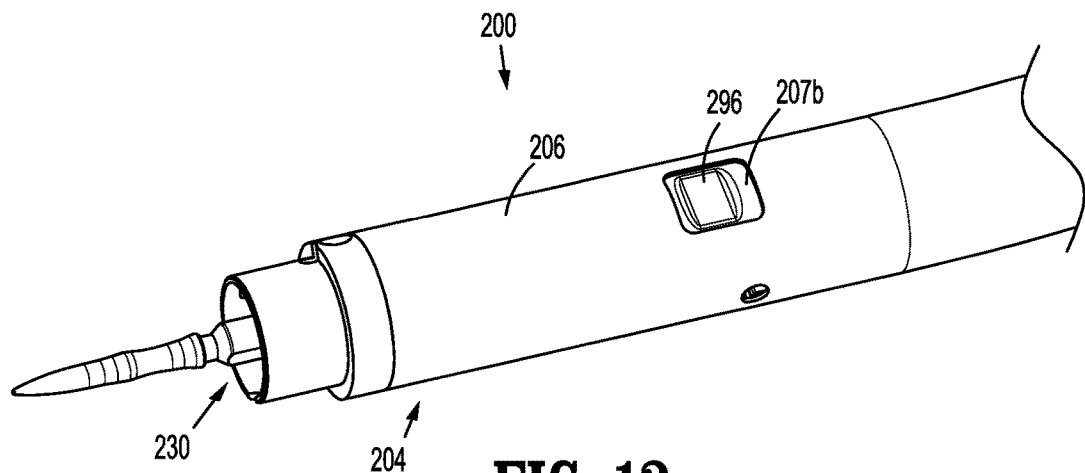
FIG. 12 is a second perspective view of the distal portion of the adapter assembly shown in FIG. 11.

With reference to FIG. 10, with the center beam 176 of the button member 170 is in the flexed position, the button member 170 is able to be depressed, as indicated by arrows "B". Depression of the button member 170 causes the cam wire 150 to move from its first position (FIG. 7) to its second position, as indicated by arrows "C". As the cam wire 150 moves to the second position, engagement of the angled portions 156*a*, 156*b* of the first and second legs 154*a*, 154*b*, respectively, with the respective first and second retainer members 180*a*, 180*b* cause the first and second retainer members 180*a*, 180*b* to move radially outward, as indicated by arrows "D". Radial outward movement of the first and second retaining members 180*a*, 180*b* withdraws the first and second retaining members 180*a*, 180*b* from within the respective first and second locking openings 123*a*, 123*b* of the trocar housing 122 of the trocar assembly 120 to permit removal of the trocar assembly 120 from within the distal portion 104 of the adapter assembly 100 (FIG. 2).

Figure 13:
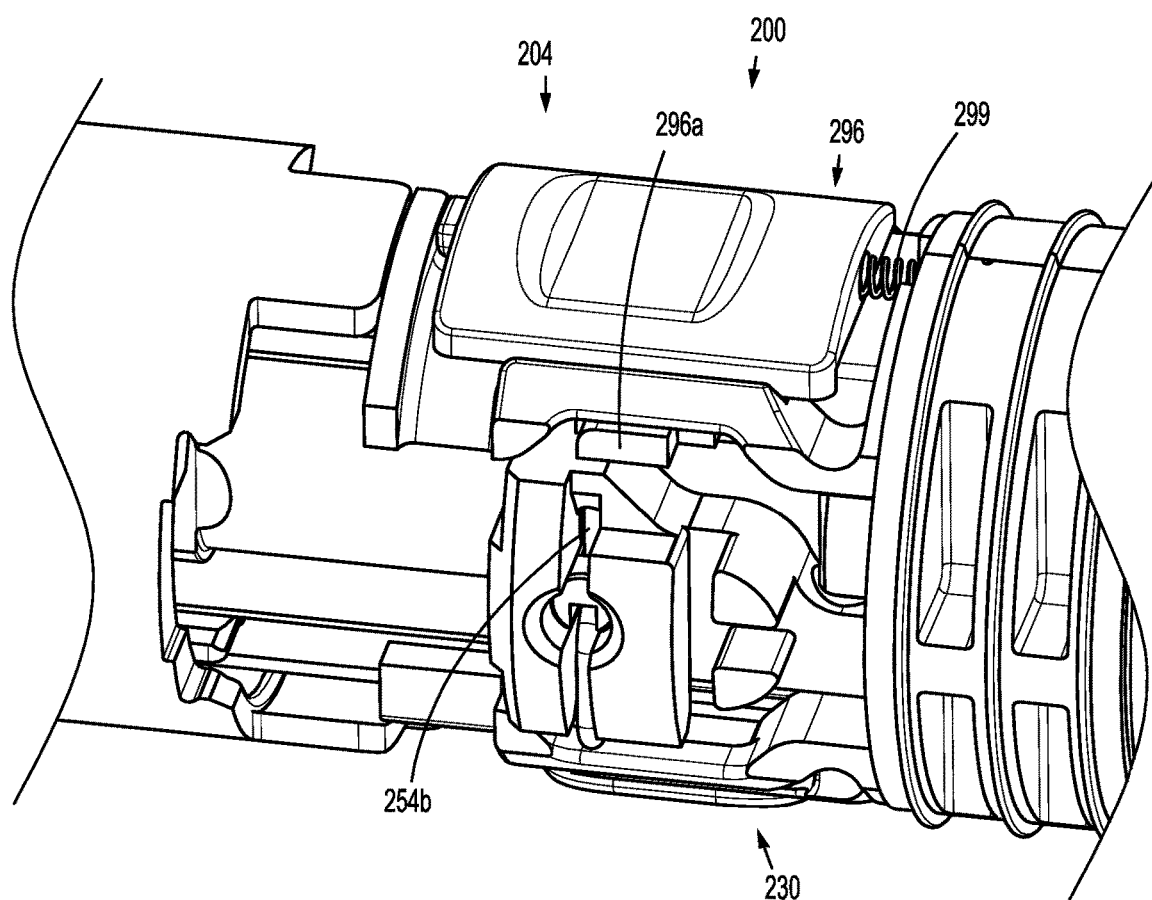
FIG. 13 is a perspective view of the distal portion of the adapter assembly shown in FIG. 11, with an outer sleeve removed to expose a retaining mechanism.

FIGS. 11-18 illustrate another embodiment of a retaining mechanism according to the disclosure shown generally as retaining mechanism 230 (FIG. 13). The retaining mechanism 230 is substantially similar to the retaining mechanism 130 described hereinabove and will only be described in detail with regards to the differences therebetween. The retaining mechanism 230 releasably secures a trocar assembly 220 within a distal portion 204 of an adapter assembly 200. The trocar assembly 220 includes a trocar housing 222 (FIG. 16) defining first and second locking openings 223*a*, 223*b* for receiving retaining members 280*a*, 280*b* (FIG. 16), respectively, of the retaining mechanism 230.

Figure 14:
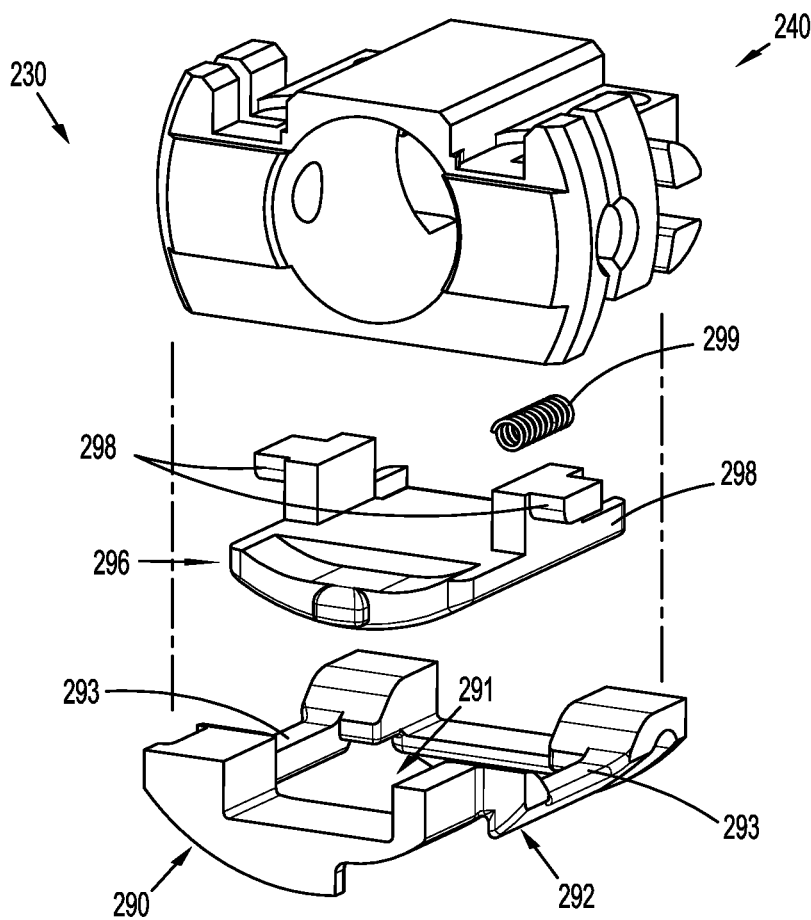
FIG. 14 is a side perspective view of the retaining mechanism shown in FIG. 13, with components separated, and a cam wire, an upper retaining member, and a button member removed.

With particular reference to FIGS. 13 and 14, the retaining mechanism 230 of the access assembly 200 includes a retaining block 240 (FIG. 13), a cam wire 250 (FIG. 16) moveably positioned relative to the retaining block 240, an upper retaining block extension 260 securing the cam wire 250 relative to the retaining block 240, a button member 270 pivotally supported by the upper retaining block 260 and in operable engagement with the cam wire 250, first and second retaining members 280*a*, 280*b* in operable engagement with the cam wire 250 and moveably disposed within the retaining block 230, a lower retaining block extension 290 disposed opposite the upper retaining block 260 in engagement with the retaining block 240, and a sliding button member 296 slidably supported on the lower retaining block extension 290.

The retaining block 240, cam wire 250, and first and second retaining members 280*a*, 280*b* of the retaining mechanism 230 of the access assembly 200 are substantially similar to the retaining block 140, cam wire 150, and first and second retaining members 180*a*, 180*b* described above. The upper retaining block extension 260 and the button member 270 are also substantially similar to the retaining block extension 160 and the button member 170. The button member 270 of the retaining mechanism 230 is accessible through a first opening 207 (FIG. 11) in an outer sleeve 206 of the adapter assembly 200. The sliding button member 296 is accessible through a second opening 207*b* (FIG. 12) in the outer sleeve 206.

Figure 15:
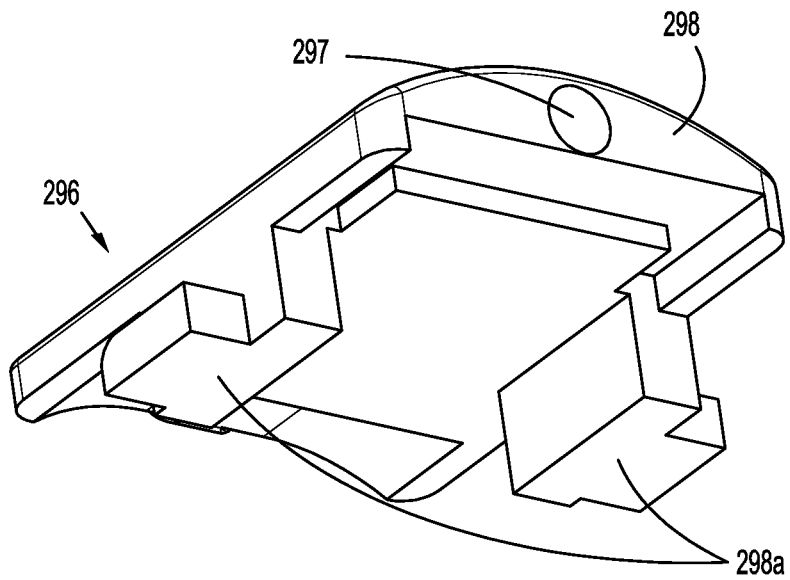
FIG. 15 is a perspective view of a lower retaining block extension of the retaining mechanism shown in FIG. 13.

FIGS. 14 and 15 illustrate the lower retaining block extension 290 of the retaining mechanism 230 which includes a substantially rectangular frame 292 defining an opening 291 for receiving the sliding button member 296. A pair of cutouts 293 in the frame 292 support a pair of stop members 298*a* of the sliding button member 296. The lower retaining block extension 290 is received within the outer sleeve 206 (FIG. 16) of the adapter assembly in engagement with the retaining block 240 and opposite the upper retaining block extension 260.

The sliding button member 296 of the retaining mechanism 290 includes a body portion 298 configured for operable engagement by a user, and the pair of stop members 298*a* extending outwardly from the body portion 298. The stop members 298*a* ride within the cutouts 293 of the lower retaining block extension 290. The sliding button member 296 is moveable between a first or distal position (FIG. 13) in which the stop members 298*a* of the sliding button member 296 are aligned with free ends 258*a*, 258*b* (FIG. 16) of legs 254*a*, 254*b*, respectively, of the cam wire 250 and a second or proximal position (FIG. 17) in which the stop members 298a are spaced from the free ends 258a, 258b of the legs 254a, 254b, respectively, of the cam wire 250.

A cylindrical recess 297 (FIG. 15) in an end of the sliding button member 296 of the retaining assembly 230 is configured to receive a biasing member, e.g., a coil spring 299 (FIG. 14) for biasing the sliding button member 296 in a first direction, e.g., distally, as shown, to the distal position. The sliding button member 296 is accessible through the second opening 207b (FIG. 12) in the outer sleeve 206 of the adapter assembly 200.

Figure 16:
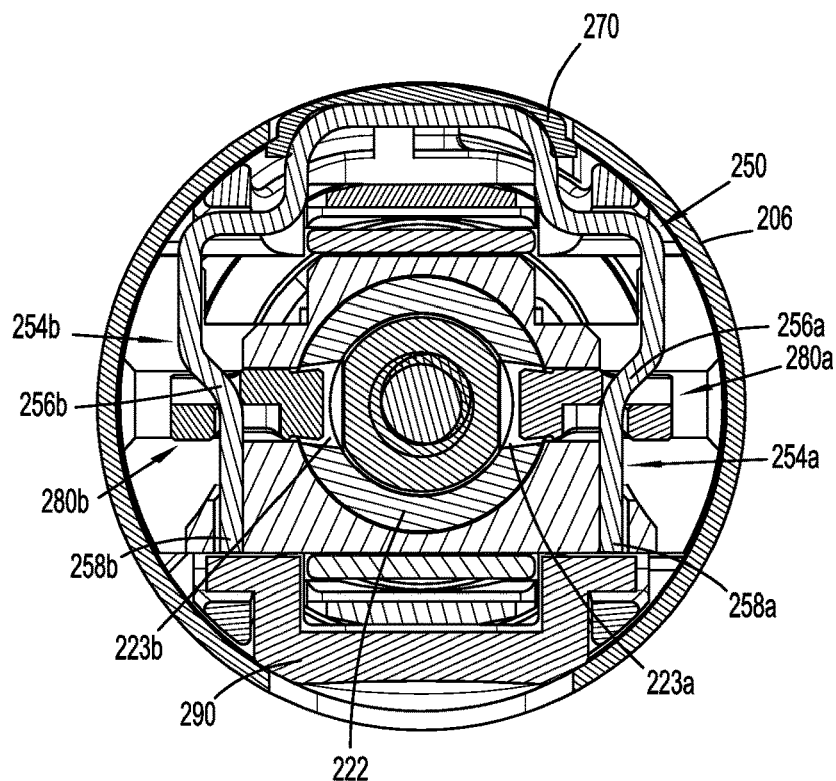
FIG. 16 is a cross-sectional end view of the adapter assembly shown in FIG. 11 taken along line 16-16 of FIG. 11.

FIG. 16 illustrates the retaining mechanism 230 in a first or lock position with the cam wire 250 in a first position and the sliding button member 296 in the distal position. The sliding button member 296 is maintained in the distal position by the coil spring 299. As described above, when the sliding button member 296 of the retaining mechanism 230 is in the proximal position, the stop members 298a of the sliding button member 298 are aligned with the free ends 258a, 258b of the legs 254a, 254b, respectively, of the cam wire 250 to prevent movement of the cam wire 250 to the second position.

Figure 17:
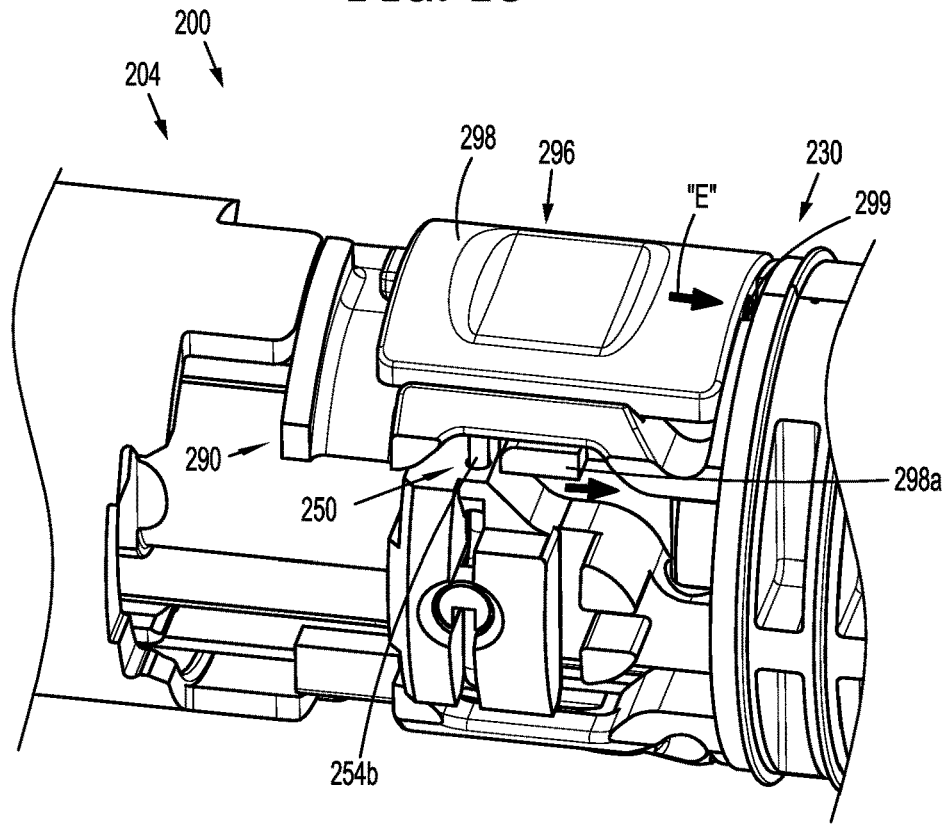
FIG. 17 is the perspective view of the distal portion of the adapter assembly shown in FIG. 13, with a sliding button member of the retaining mechanism shown in FIG. 13 in a proximal position.
Figure 18:
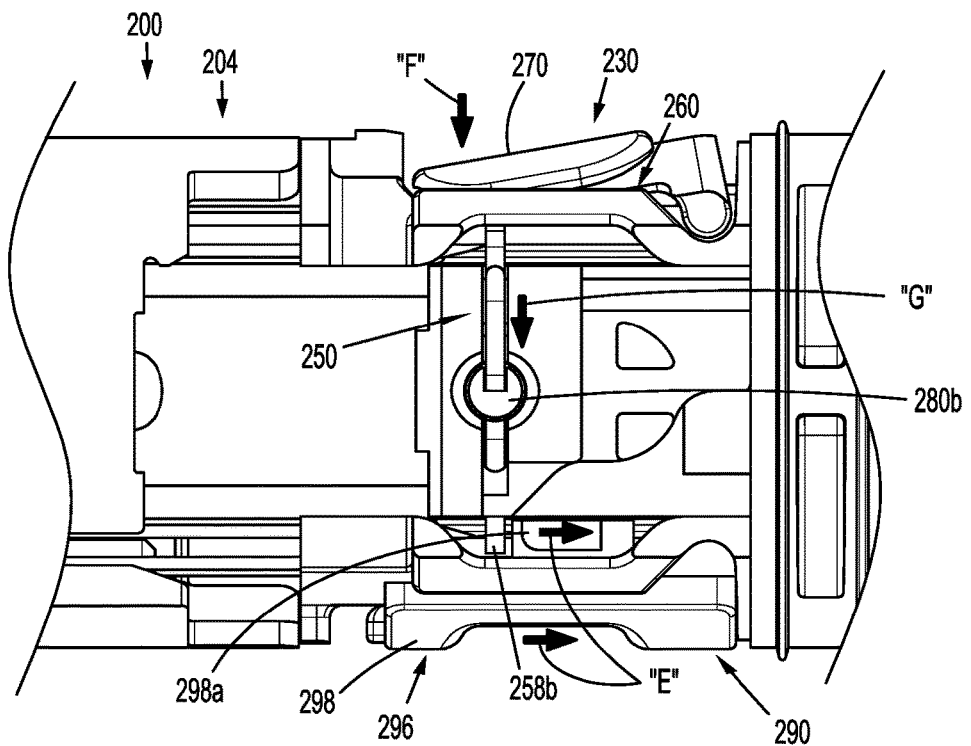
FIG. 18 is a side view of the retaining mechanism shown in FIG. 17, with the sliding button member in the proximal position and the button member in a depressed condition.
Figure 19:
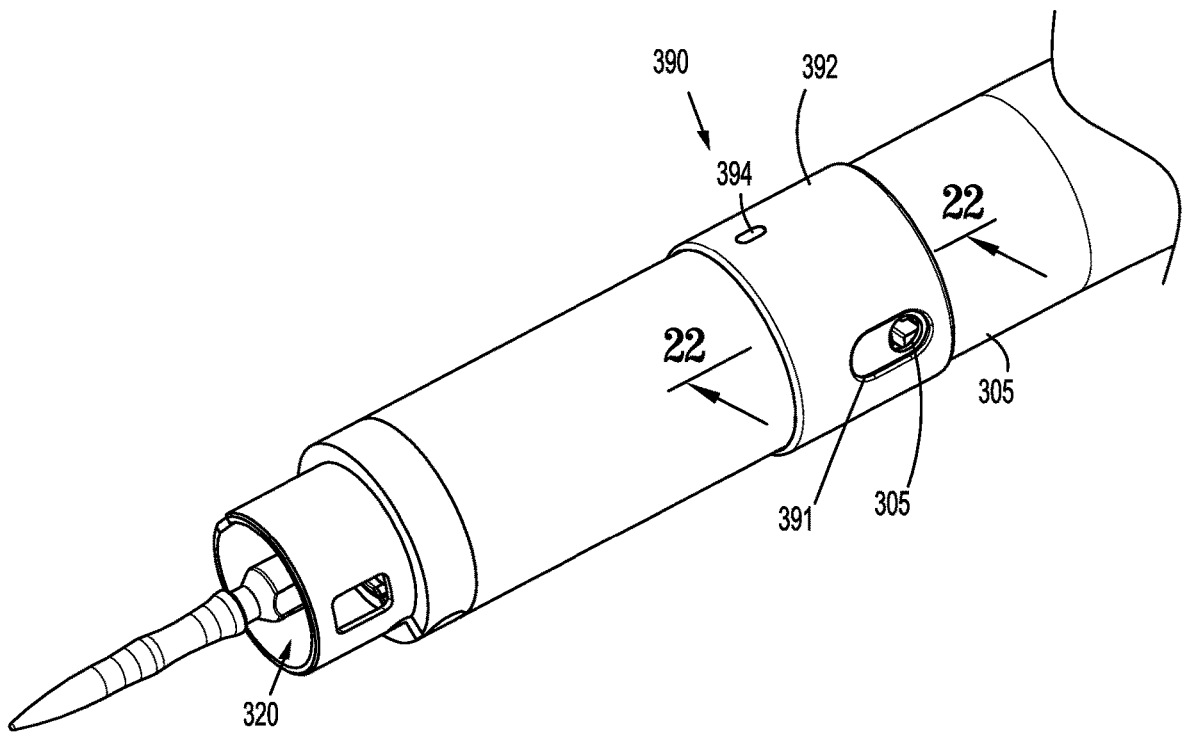
FIG. 19 is a distal portion of an adapter assembly according to another exemplary embodiment of the disclosure including a collar assembly.
Figure 20:
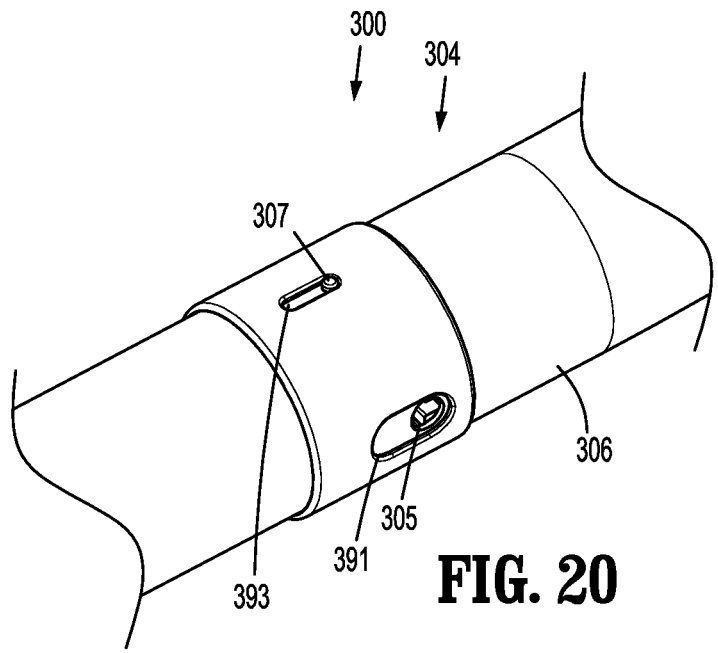
FIG. 20 is another perspective side view of a portion of the distal portion of the adapter assembly shown in FIG. 19.
Figure 21:
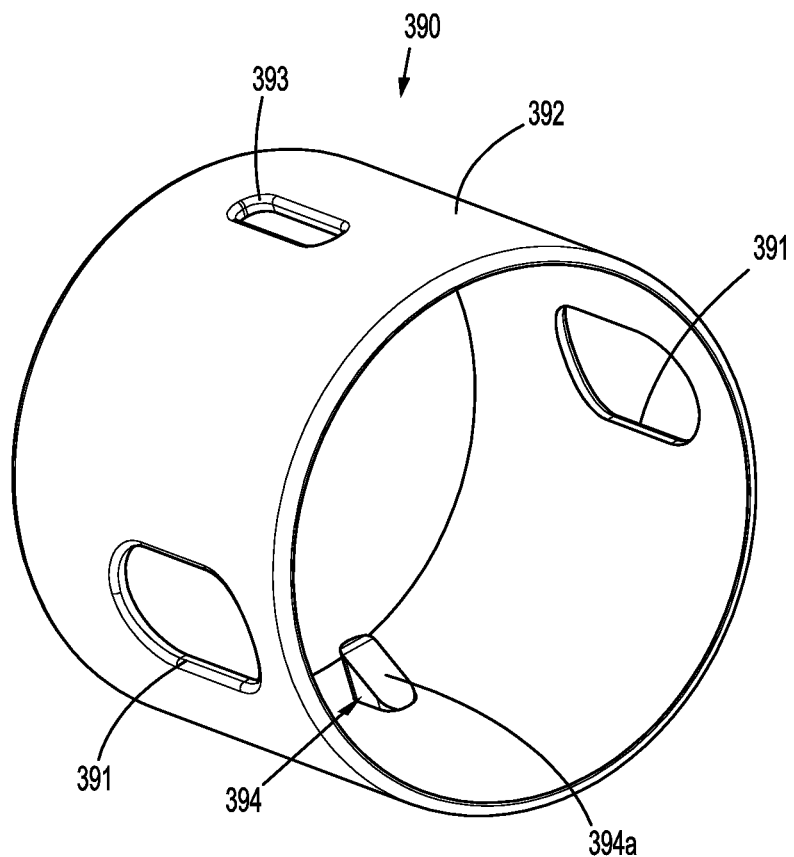
FIG. 21 is a perspective side view of the collar assembly shown in FIG. 19.

FIGS. 17 and 18 illustrate the method for removal of the trocar assembly 230 from the adaptor assembly 200. When the trocar assembly 230 is removed from the distal portion 204 of the adapter assembly 200, the sliding button member 296 is moved proximally, against the bias of the coil spring 299, as indicated by arrows "E". Proximal movement of the sliding button member 296 moves the stop members 298a of the sliding button member 296 out of engagement with the free ends 258a, 258b (FIG. 16) of the legs 254a, 254b, respectively, of the cam wire 250. With the stop members 298a of the sliding button member 296 no longer preventing movement of the cam wire 250 to the second position, the button member 270 may be depressed, as indicated by arrow "F" to cause the cam wire 250 to move to the second position, as indicated by arrows "G". As discussed in detail above with respect to retaining mechanism 130, as the cam wire 250 moves to the second position, the retaining members 280a, 280b (FIG. 16) move radially outward from within first and second locking openings 223a, 223b of a trocar housing 232 of the trocar assembly 230 to release the trocar assembly 230 from within the distal portion 204 of the adapter assembly 200, and permit removal of the trocar assembly 230 from within the adapter assembly 200.

FIGS. 19-25 illustrate a release mechanism according to another exemplary embodiment of the disclosure. The release mechanism is shown generally as collar assembly 390. The collar assembly 390 is configured to depress a button member 370 of a trocar retaining mechanism 320. More particularly, collar assembly 390 includes an annular member 392 receivable about a distal portion 304 of an adapter assembly 300. The annular member 392 includes a cam lug 394 extending from an inner surface of the annular member 392 and having an inclined surface 394. The cam lug 394 is configured to engage and depress the button member 370 during proximal movement of the collar assembly 390 relative to the outer sleeve 306 of the adapter assembly 300.

The annular member 392 defines a pair of flush ports 391 (FIG. 21), and a slot 393 for receiving a pin 307 extending from an outer sleeve 306 of the adapter assembly 300. The flush ports 391 align with a flush port 305 on the outer sleeve 306 of the adapter assembly 300. The pin 307 limits travel of the collar assembly 390 relative to the adapter assembly 300.

Figure 22:
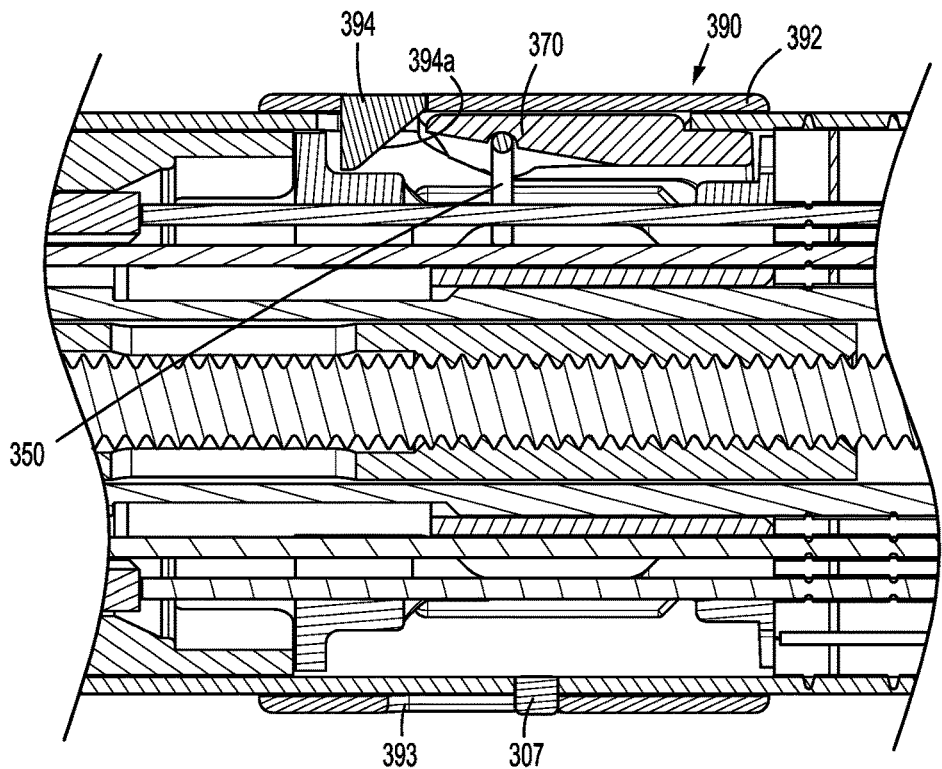
FIG. 22 is a cross-sectional side view of the adapter assembly taken along line 22-22 of FIG. 19, with the collar assembly in a distal position.

With particular reference to FIG. 22, the collar assembly 390 is shown in a first or distal position. In the distal position, the cam lug 394 is spaced from the button member 370. In this manner, the button member 370 is in a first or undepressed position. When the collar assembly 390 is in the distal position, the annular member 392 covers the button member 370 to prevent accidental depression of the button member 370. In embodiments, the collar assembly 390 may be maintained in the distal position by a biasing member, e.g., coil spring 399 (FIG. 24), received about the outer sleeve 306 of the adapter assembly 300 proximal of the collar assembly 390. It is envisioned that the collar assembly 390 may be biased distally using a pneumatic cylinder, or in any other suitable manner.

Figure 23:
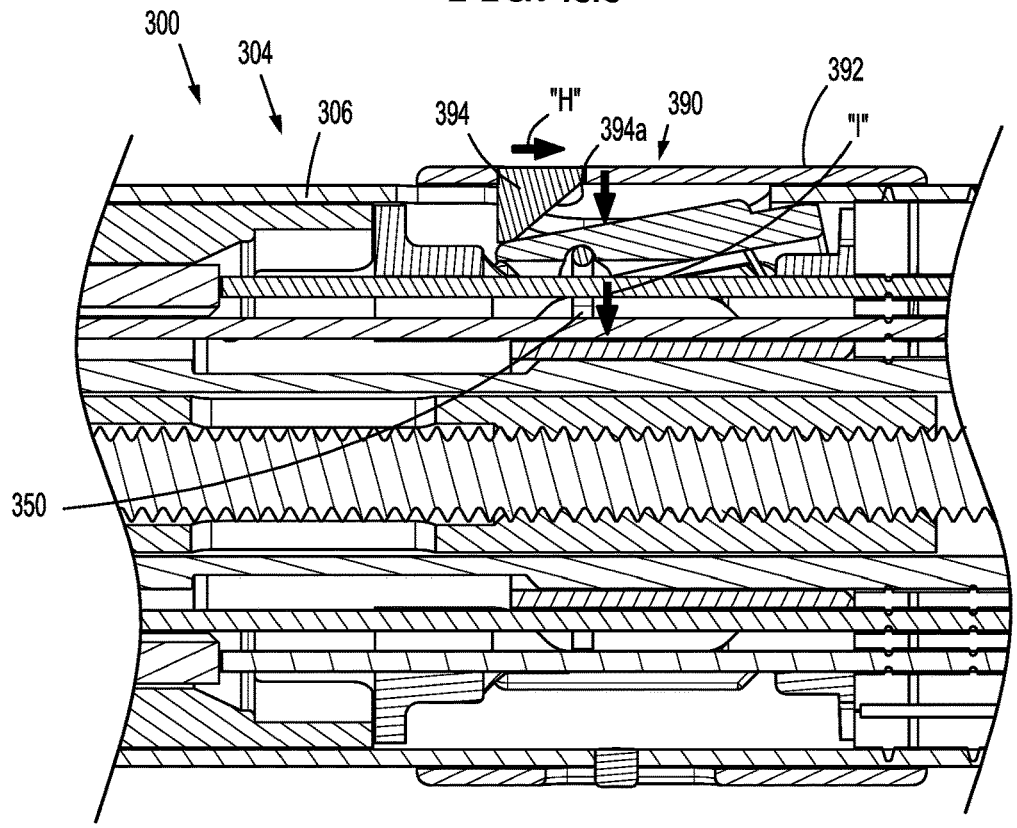
FIG. 23 is the cross-sectional side view shown in FIG. 22, with the collar assembly in a proximal position.
Figure 24:
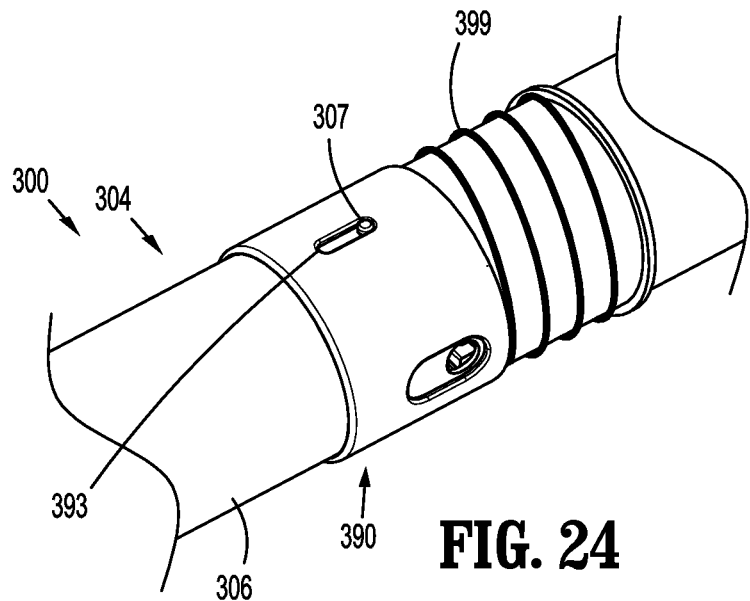
FIG. 24 is a perspective side view of an adapter assembly according to yet another exemplary embodiment of the disclosure including a collar assembly and a biasing member for maintaining the collar assembly in a proximal position.

FIG. 23 illustrates the collar assembly 390 as it is moved proximally as indicated by arrows "H". When the collar assembly 390 is moved proximally, as indicated by arrows "H", the inclined surface 394a of the cam lug 394 of the collar assembly 390 engages the button member 370, causing the button member 370 to be depressed, as indicated by arrow "I". As the button member 370 is depressed, the cam wire 350 is moved to a second position to cause the release of trocar assembly 320 as described above with reference to retaining mechanism 130 and trocar assembly 120. As noted above, the pin 307 (FIG. 24) extending from the outer sleeve 306 of the adapter assembly 300 limits travel of the collar assembly 390.

Figure 25:
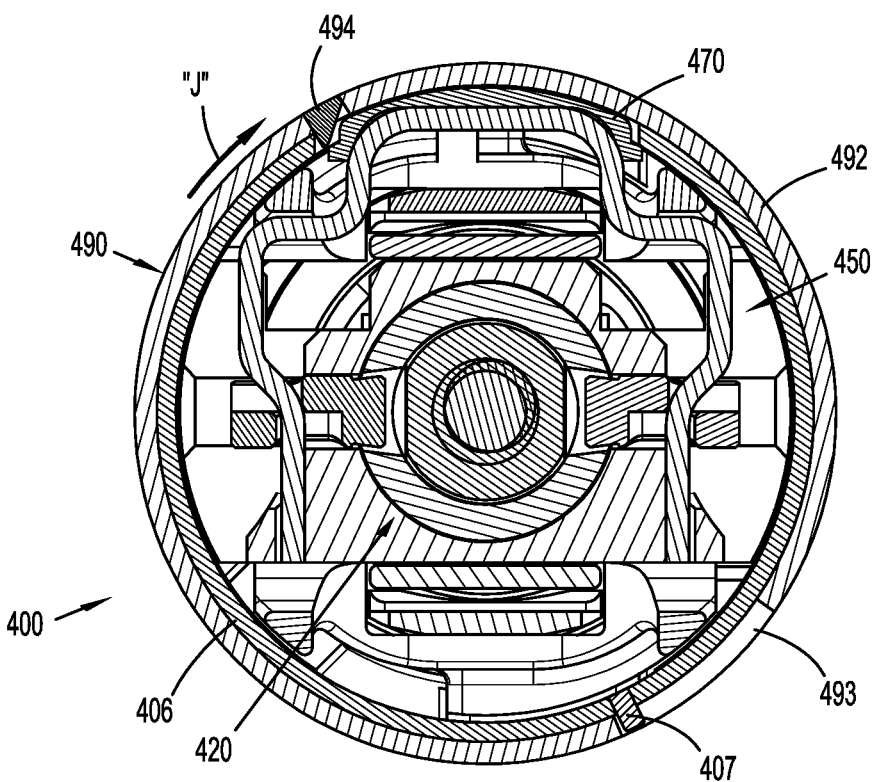
FIG. 25 is a cross-sectional end view of an adapter assembly according to another exemplary embodiment of the disclosure including a collar assembly.

With reference to FIG. 25, in an alternative embodiment, a collar assembly 490 is configured to be rotated relative to the outer sleeve 406 of the adapter assembly 400 to effect depression of a button member 470 of the retaining assembly 430. The collar assembly 490 includes an annular member 492 and a cam lug 494 extending from an inner surface of the annular member 492. The cam lug 494 is configured to engage the button member 470 and defines a slot 493 for receiving a pin 407. The pin 407 extends from the outer sleeve 406 for limiting movement of the collar assembly 490.

During use, the collar assembly 490 is rotated about the outer sleeve 406 of the adapter assembly 400, as indicated by arrow "J". When the cam lug 496 of the collar assembly 490 engages the button member 496, the button member 496 is depressed, causing a wire cam 450 to move to a second or release position, thereby unlocking a trocar assembly 420 received within the adapter assembly 400.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the disclosure. As well, one skilled in the art will appreciate further features and advantages of the disclosure based on the above-described embodiments. Accordingly, the disclosure is not to be limited by what has been particularly shown and described.

What is claimed is:

1. An adapter assembly for connecting a loading unit to a handle assembly, the adapter assembly comprising:
    an outer sleeve;
    a trocar assembly releasably securable within the outer sleeve, the trocar assembly including a trocar housing defining first and second openings; and
    a retaining mechanism configured to releasably secure the trocar assembly within the outer sleeve, the retaining mechanism including a retaining block, a cam wire moveably positioned relative to the retaining block between a lock position and a release position, a retaining block extension configured to maintain the cam wire relative to the retaining block, a button member in operable engagement with the cam wire, and a pair of retaining members moveable from a first position received within the first and second openings of the trocar assembly when the cam wire is in the lock position and a second position spaced from the trocar assembly when the cam wire is in the release position, the retaining block extension including a stop tab, wherein the button member includes a center beam moveable from an unflexed position in engagement with the stop tab of the retaining block extension to prevent movement of the button member to a flexed position out of alignment with the stop tab to permit movement of the button member.

2. The adapter assembly of claim 1, wherein the button member is pivotable relative to the retaining block from a non-depressed position when the center beam is in the unflexed position and a depressed position when the center beam is in the flexed position.

3. The adapter assembly of claim 2, wherein depression of the button member causes the cam wire to move from the lock position to the release position.

4. The adapter assembly of claim 2, wherein the center beam includes a rib configured for operable engagement by a user.

5. The adapter assembly of claim 2, wherein the button member defines a relief on either side of the center beam to permit movement of the center beam between the unflexed and flexed positions.

6. The adapter assembly of claim 2, wherein the button member defines a midline, the stop tab being aligned with the midline.

7. The adapter assembly of claim 6, wherein the center beam is aligned with the midline when in the unflexed position and is misaligned with the midline when in the flexed position.

8. The adapter assembly of claim 1, wherein the retaining block defines a central opening for receiving the trocar assembly.

9. The adapter assembly of claim 1, wherein each retaining member of the pair of retaining members include a wedge-shaped free end.

10. The adapter assembly of claim 1, wherein the retaining block defines a central opening for receiving the trocar assembly.

11. An adapter assembly for connecting a loading unit to a handle assembly, the adapter assembly comprising:
an outer sleeve; and
a retaining mechanism configured to releasably secure a trocar assembly within the outer sleeve, the retaining mechanism including a retaining block defining a longitudinal passage for receipt of the trocar assembly, a cam wire moveably positioned relative to the retaining block between a lock position and a release position, a retaining block extension configured to maintain the cam wire relative to the retaining block, a button member in operable engagement with the cam wire, and at least one retaining member moveable from a first position extending into the longitudinal passage when the cam wire is in the lock position and a second position clear of the longitudinal passage when the cam wire is in the release position, the retaining block extension including a stop member, wherein the button member includes a flexible portion moveable from an unflexed position in engagement with the stop member of the retaining block extension to prevent movement of the button member to a flexed position out of alignment with the stop member to permit movement of the button member.

12. The adapter assembly of claim 11, wherein the button member is pivotable relative to the retaining block from a non-depressed position when the flexible portion is in the unflexed position to a depressed position when the center beam is in the flexed position.

13. The adapter assembly of claim 12, wherein depression of the button member causes the cam wire to move from the lock position to the release position.

14. The adapter assembly of claim 12, wherein the flexible portion includes a rib configured for operable engagement by a user.

15. The adapter assembly of claim 12, wherein the button member defines a relief on either side of the flexible portion to permit movement of the flexible portion between the unflexed and flexed positions.

16. The adapter assembly of claim 12, wherein the button member defines a midline, the stop member being aligned with the midline.

17. The adapter assembly of claim 16, wherein the flexible portion is aligned with the midline when in the unflexed position and the flexible portion is misaligned with the midline when in the flexed position.

18. The adapter assembly of claim 11, wherein the retaining block defines a central opening for receiving the trocar assembly.

19. The adapter assembly of claim 11, wherein each retaining member of the pair of retaining members include a wedge-shaped free end.

20. An adapter assembly for connecting a loading unit to a handle assembly, the adapter assembly comprising:
an outer sleeve; and
a retaining mechanism configured to releasably secure a trocar assembly within the outer sleeve, the retaining mechanism including a retaining block, a cam wire moveably positioned relative to the retaining block between a lock position and a release position, a retaining block extension configured to maintain the cam wire relative to the retaining block, a button member in operable engagement with the cam wire, and a pair of retaining members moveable from a first position engageable with the trocar assembly when the trocar assembly is received within the outer sleeve and the cam wire is in the lock position, and a second position spaced from the trocar assembly when the trocar assembly is received within the sleeve and the cam wire is in the release position, the retaining block extension including a stop member, wherein the button member includes a center beam moveable from an unflexed position in engagement with the stop member of the retaining block extension to prevent movement of the button member to a flexed position out of alignment with the stop member to permit movement of the button member.

* * * * *